United States Patent
LaBorde

(10) Patent No.: US 10,354,750 B2
(45) Date of Patent: *Jul. 16, 2019

(54) SYSTEM, CLIENT DEVICE, SERVER AND METHOD FOR PROVIDING A CROSS-FACILITY PATIENT DATA MANAGEMENT AND REPORTING PLATFORM

(71) Applicant: David LaBorde, Tucker, GA (US)

(72) Inventor: David LaBorde, Tucker, GA (US)

(73) Assignee: ICONIC DATA INC., Norcross, GA (US)

( * ) Notice: Subject to any disclaimer, the term of this patent is extended or adjusted under 35 U.S.C. 154(b) by 998 days.

This patent is subject to a terminal disclaimer.

(21) Appl. No.: 14/613,022

(22) Filed: Feb. 3, 2015

(65) Prior Publication Data

US 2015/0169827 A1   Jun. 18, 2015

Related U.S. Application Data

(63) Continuation-in-part of application No. 13/724,163, filed on Dec. 21, 2012, now abandoned.

(Continued)

(51) Int. Cl.
*G06Q 50/00*   (2012.01)
*G16H 10/60*   (2018.01)
(Continued)

(52) U.S. Cl.
CPC ............. *G16H 10/60* (2018.01); *G06F 19/00* (2013.01); *H04L 9/0861* (2013.01);
(Continued)

(58) Field of Classification Search
CPC ........ G06Q 50/22; G06Q 50/24; G06Q 10/10; G06Q 40/08; G06F 19/322; G06F 19/321; G06F 19/326; G06F 19/328; G06F 19/3481; G06F 17/30; G06F 19/30; G06F 19/324; G06F 19/325; G06F 19/34; G06F 19/3456; G06F 19/3462; G06F 19/3468; G06F 19/3475; G06F 19/36; G06F 19/32; G06F 19/3418; A61N 1/08; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60;
(Continued)

(56) References Cited

U.S. PATENT DOCUMENTS 5,579,393 A   11/1996 Conner
7,353,238 B1   4/2008 Gliklich
(Continued)

*Primary Examiner* — Tran N Nguyen
(74) *Attorney, Agent, or Firm* — Culpepper IP, LLLC; Kerry S. Culpepper

(57) ABSTRACT

A system for providing a patient list manager includes a client device for point of care capture and access of patient data and a server for providing cloud based hosting. One or more modules can leverage the patient data to help users improve and facilitate the efficiency and safety of patient management, diagnostic imaging management, clinical work flows, charge capture, revenue cycle management, accreditation reporting, quality and outcomes monitoring and improvement, among other things.

10 Claims, 51 Drawing Sheets

Related U.S. Application Data

(60) Provisional application No. 61/579,956, filed on Dec. 23, 2011.

(51) Int. Cl.
 *H04L 29/08* (2006.01)
 *H04L 9/08* (2006.01)
 *H04L 29/06* (2006.01)
 *G06F 19/00* (2018.01)
 *G06Q 10/00* (2012.01)

(52) U.S. Cl.
 CPC .......... *H04L 63/0823* (2013.01); *H04L 67/12* (2013.01); *G06Q 2220/10* (2013.01)

(58) Field of Classification Search
 CPC ........ G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 50/80; G16H 70/00; G16H 70/20; G16H 70/14; G16H 70/60; G16H 80/00
 See application file for complete search history.

(56) References Cited

U.S. PATENT DOCUMENTS

| | | |
|---|---|---|
| 2001/0032215 A1 | 10/2001 | Kyle |
| 2002/0019749 A1 | 2/2002 | Becker et al. |
| 2002/0123907 A1 | 9/2002 | Strayer |
| 2005/0251417 A1 | 11/2005 | Malhotra |
| 2005/0288965 A1* | 12/2005 | Van Eaton ............ G06Q 10/00 705/2 |
| 2006/0053034 A1 | 3/2006 | Hlathein |
| 2006/0229911 A1* | 10/2006 | Gropper ............... G06F 19/321 705/2 |
| 2007/0143148 A1 | 6/2007 | Kol |
| 2007/0188774 A1 | 8/2007 | Yudasaka |
| 2008/0133269 A1 | 6/2008 | Ching |
| 2009/0132586 A1 | 5/2009 | Napora |
| 2009/0164236 A1 | 6/2009 | Gounares |
| 2010/0122179 A1 | 5/2010 | Nakamura |
| 2010/0161345 A1 | 6/2010 | Cain |
| 2010/0305966 A1* | 12/2010 | Coulter ................ G06Q 10/04 705/2 |
| 2011/0110568 A1 | 5/2011 | Vesper |
| 2011/0153351 A1 | 6/2011 | Vesper |
| 2012/0173281 A1 | 7/2012 | DiLella |
| 2013/0054260 A1 | 2/2013 | Evans |
| 2013/0096938 A1 | 4/2013 | Stueckemann |
| 2013/0307955 A1 | 11/2013 | Deitz |
| 2014/0015987 A1* | 1/2014 | Harple .................. G06F 3/005 348/207.1 |
| 2014/0249860 A1 | 9/2014 | Rynchek |

* cited by examiner

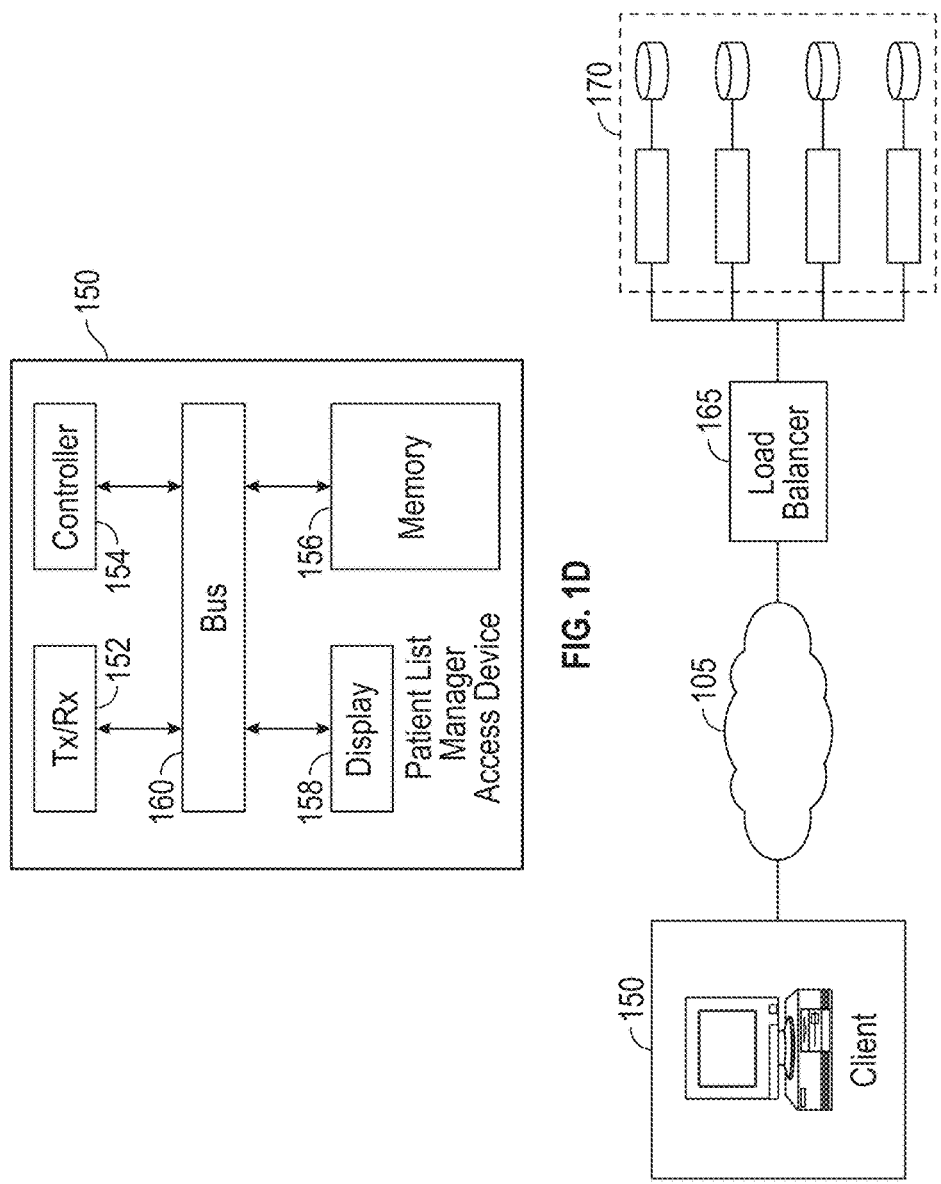

FIG. 5

| Hospital | Room | 1 | MD | Name | MRN | Age | DOA |
|---|---|---|---|---|---|---|---|
| 👤 | | | | | | 55 | |
| 👤 | | | | | | 52 | |
| ▽ 31 ICU | | | | | | | |
| 👤 | | | | | | 79 | |
| 👤 | | | | | | 39 | |
| 👤 | | | | | | 60 | |
| 👤 | | | | | | 49 | |
| 👤 | | | | | | 41 | |
| 👤 | | | | | | 56 | |
| ▽ Unit 11 | | | | | | | |
| 👤 | | | | | | 81 | |

New Patient

| | | | | |
|---|---|---|---|---|
| Patient List | Reports | Images | Admin | |

Name (First/Middle/Last): *First* *Middle* *Last*
DOB/Sex: ▦ Age: n/a Select Sex ▽
MRN/Location: MRN Room Select Hospital... ▽ Select Floor... ▽
Encounter Type/Date: Select Encounter Type... ▦ Today
Attending: Select Attending... ▽
Diagnosis/Details: Select Diagnosis... ▽ Diagnosis details (max 35 characters to prevent pdf wrapping) Chars: 0
  Altered mental status (AMS)
  Aneurysm-Non-ruptured (rysm)
  Arachroid cyst (Arach Cyst)
  Astrocytoma (Astro)
  Aterovenous Fistula (AVF)
  Aterovenous Malformation (AVM)
  Back Pain (Back pain)
  Basilar artery thrombosis (BA thromb)
  Brain Lesion (Brain Mass)
  Brain Metastatic Lesion (Brain Met)
  Carcinomatous Meningitis (Carciro mgtis)
  Carotid occlusion (Carotid Occ)
  Carotid stenosis (Carotid Sten)
Procedures:

FIG. 12

New Patient

| Patient List | Reports | Images | Admin |
|---|---|---|---|

Name (First/Middle/Last): [First] [Middle] [Last]

DOB/Sex: [ ] 🗓 Age: n/a [Select Sex ▽]

MRN/Location: [MRN] [Room] [Select Hospital... ▽] [Select Floor... ▽]

Encounter Type/Date: [Select Encounter Type...] 🗓 [Today]

Attending: [Select Attending... ▽]

Diagnosis/Details: Subarachnoid hemorrhage, Hunt and Hess 1 (SAHH) [SAHHH1 (1/28), R MCA]

Procedures:

| Date | Procedure | POD | | |
|---|---|---|---|---|
| 01/24/2011 | Crani | 0 | | |
| | | | | |
| | | | | |
| | | | | |

[+] [−]

Date: [01/24/2011] 🗓 [Today]

Procedure: Craniotomy | Neurovascular | Aneurysm clipping | Pterional (Crani) ▽

Detail: [01/24-Crani01/24-Coil] Chars: 21

Physicians:

| Physician | Role |
|---|---|
| | Attending |
| | Fellow |
| | Resident |

[+] [−]

[Save Procedures]

Remove Patient

Disposition Type: | Discharged ▽ |
Disposition Date: | 01/24/2011 | 🗓
Morbidity: ☑
Complications: | CSF Leak |

[Cancel] [Submit]

FIG. 19

| Patient List | Encounter Query | Admin |

Administrative Panel

Audit Log
Diagnoses
Disposition Types
Encounter Types
Facilities
Physician Groups
Procedures
Unit Types
Users Search: ☐

| Timestamp ▽ | Description ◇ | Type ◇ | IP Address ◇ | User ◇ |
|---|---|---|---|---|
| 16 Dec-2011 06:51:56 AM EST | viewed admin panel | VIEW | 76.122.90.114 | LaBorde, David |
| 16 Dec-2011 06:51:35 AM EST | ran encounter query with parameters: fromDate=null toDate=null procFromDate=null procToDate=null encTypeID=1 facilityID=3 admittingID=null dispoTypeID=null morbidity=all | QUERY | 76.122.90.114 | LaBorde, David |
| 16 Dec-2011 06:51:10 AM EST | ran encounter query with parameters: fromDate=null toDate=null procFromDate=null procToDate=null encTypeID=1 facilityID=5 admittingID=null dispoTypeID=null morbidity=all | QUERY | 76.122.90.114 | LaBorde, David |
| 16 Dec-2011 06:51:59 AM EST | ran encounter query with parameters: fromDate=null toDate=null procFromDate=null procToDate=null encTypeID=1 facilityID=4 admittingID=null dispoTypeID=null morbidity=all | QUERY | 76.122.90.114 | LaBorde, David |
| 16 Dec-2011 06:50:45 AM EST | ran encounter query with parameters: fromDate=null toDate=null procFromDate=null procToDate=null encTypeID=1 facilityID=1 admittingID=null dispoTypeID=null morbidity=all | QUERY | 76.122.90.114 | LaBorde, David |
| 16 Dec-2011 06:40:45 AM EST | viewed current encounters | VIEW | 76.122.90.114 | LaBorde, David |
| 16 Dec-2011 06:40:31 AM EST | | | | |

FIG. 20A

| Patient List | Encounter Query | Admin |

Administrative Panel

Audit Log
Diagnoses
  Disposition Types
  Encounter Types
  Facilities
  Physician Groups
  Procedures
  Unit Types
  Users Add Diagnosis Search: _____

| Name ◇ | Shorthand ◇ | ICDS ◇ | Active ◇ | Edit ◇ | Delete ◇ |
|---|---|---|---|---|---|
| Adenovirus Enteritis | AE | 8.62 | ☑ | Edit | Delete |
| Aerobacter Enteritis | AeE | 8.2 | ☑ | Edit | Delete |
| Altered mental status | AMS | 286.0 | ☑ | Edit | Delete |
| Amebiasis | Ame | 6 | ☑ | Edit | Delete |
| Amebiasis Nos | AN | 6.9 | ☑ | Edit | Delete |
| Amebic Brain Abscess | ABA | 6.5 | ☑ | Edit | Delete |
| Amebic Liver Abscess | ALA | 6.3 | ☑ | Edit | Delete |
| Aneurysm - Non - Ruptured | nysm | 283.1 | ☐ | Edit | Delete |
| Anisocoria | Anisocoria | 282.3 | ☑ | Edit | Delete |
| Bacterial Enteritis Nec | BFPN | 8.4 | ☑ | Edit | Delete |
| Bacterial Enteritis Nos | BFPNos | 8.5 | ☑ | Edit | Delete |
| Bad Food Poisoning Nec | BFPN | 5.8 | ☑ | Edit | Delete |
| Bad Food Poisoning Nec | BFPN | 5.89 | ☑ | Edit | Delete |
| Balantidiasis | Bal | 7 | ☑ | Edit | Delete |
| Botulism Food Poisoning | BFP | 5.1 | ☑ | Edit | Delete |
| C. Difficile Enteritis | CDE | 8.45 | ☑ | Edit | Delete |
| Camoylobacter Enteritis | CE | 8.43 | ☑ | Edit | Delete |

FIG. 21

| Patient List | Encounter Query | Admin |

Administrative Panel

Audit Log
Diagnoses
Disposition Types
Encounter Types
Facilities
Physician Groups
Procedures
Unit Types
Users Add Disposition Type Search:

| Name | Active | | | |
|---|---|---|---|---|
| Acute | ☑ | Edit | | Delete |
| Died | ☑ | Edit | | Delete |
| Escaped | ☑ | Edit | | Delete |
| Home | ☑ | Edit | | Delete |
| Rehab | ☑ | Edit | | Delete |
| Sign Off | ☑ | Edit | | Delete |
| Subacute Rehab | ☑ | Edit | | Delete |

FIG. 22

| Patient List | Encounter Query | Admin |

Administrative Panel

Audit Log
Diagnoses
Disposition Types
Encounter Types
Facilities
Physician Groups
Procedures
Unit Types
Users Add Encounter Type Search:

| Name | | Consult | ◊ | Active | ◊ | Edit | ◊ | Delete | ◊ |
|---|---|---|---|---|---|---|---|---|---|
| Admission | | ☐ | | ☑ | | Edit | | Delete | |
| Clinic (Outpt Visit) | | ☐ | | ☑ | | Edit | | Delete | |
| Consult Inpt | | ☑ | | ☑ | | Edit | | Delete | |
| Consult - ED Inpt | | ☑ | | ☑ | | Edit | | Delete | |
| Consult - ED Outpt | | ☑ | | ☑ | | Edit | | Delete | |
| Consult - Neurology Inpt | | ☑ | | ☑ | | Edit | | Delete | |
| Consult - Neurology Outpt | | ☑ | | ☑ | | Edit | | Delete | |

FIG. 23

| Patient List | Encounter Query | Admin |

Administrative Panel

- Audit Log
- Diagnoses
- Disposition Types
- Encounter Types
- Facilities
- Physician Groups
- Procedures
- Unit Types
- Users Add Facility Search: _____

| Name ◁ | Shorthand ◇ | Active ◇ | | |
|---|---|---|---|---|
| Children's Healthcare of Alpha Zion | CHOAZ | ☑ | Edit | Delete |
| Children's Healthcare of New Atlantis | CHONA | ☑ | Edit | Delete |
| Gaia Prime University Hospital | GPUH | ☑ | Edit | Delete |
| Ivory Seven University Hospital | ISUH | ☑ | Edit | Delete |
| Terra Memorial Hospital | TMH | ☑ | Edit | Delete |

FIG. 24

| Patient List | Encounter Query | Admin |

Administrative Panel

- Audit Log
- Diagnoses
- Disposition Types
- Encounter Types
- Facilities
- Physician Groups
- Procedures
- Unit Types
- Users Add Physician Group

| Name ▽ | Shorthand ◇ | Active ◇ | Edit ◇ | Search: | |
|---|---|---|---|---|---|
| Cerebral Vascular | CV | ☑ | Edit | Show Members ◇ | Delete ◇ |
| Functional One | Func/One | ☑ | Edit | Show Members | Delete |
| | | | | Hide Members | Delete |

Barret, Danny L.  Add Member

| Boss, Niko M. (NMB) | Remove |
| Grant, Robert E. (REG) | Remove |
| Holiday, Constantine G. (CGH) | Remove |
| Law, Jaya (JL) | Remove |
| Rifle, Dope (DR) | Remove |

FIG. 25

| Patient List | Encounter Query | Admin |

Administrative Panel

Audit Log
Diagnoses
Disposition Types
Encounter Types
Facilities
Physician Groups
Procedures
Unit Types
Users Add Procedure Search: [    ]

| Name ▲ | Shorthand ◇ | Active ◇ | Edit ◇ | Delete ◇ |
|---|---|---|---|---|
| Angioplasty | Plasty | ☑ | Edit | Delete |
| Angioplasty / IA Verapamil | Plasty/IAV | ☑ | Edit | Delete |
| Anterior Lumbar Interbody Fusion | ALIF | ☑ | Edit | Delete |
| Really Long, Long XX, Anterior Lumbar Interbody Fusion Name | long | ☐ | Edit | Delete |

FIG. 26

| Patient List | Encounter Query | Admin |

Administrative Panel

- Audit Log
- Diagnoses
- Disposition Types
- Encounter Types
- Facilities
- Physician Groups
- Procedures
- Unit Types
- Users Add Unit Type Search:

| Name △ | Active ○ | Edit ○ | Delete ◇ |
|---|---|---|---|
| Consult | ☑ | Edit | Delete |
| Ectopic | ☑ | Edit | Delete |
| Floor | ☑ | Edit | Delete |
| IC | ☑ | Edit | Delete |
| MedSurg | ☑ | Edit | Delete |
| Unit | ☑ | Edit | Delete |

FIG. 27

| Patient List | Encounter Query | Admin |

Administrative Panel

- Audit Log
- Diagnoses
- Disposition Types
- Encounter Types
- Facilities
- Physician Groups
- Procedures
- Unit Types
- Users Add User Search: _____

| Name ▲ | Initials ◇ | E-Mail ◇ | Last Login ◇ | Physician ◇ | Admin ◇ | Active ◇ | Edit ◇ |
|---|---|---|---|---|---|---|---|
| Howard, Buster | BH | bh@gmail.com | | ☑ | ☐ | ☐ | Edit |
| Ichimaru, Adriana | AI | ai@gmail.com | | ☑ | ☐ | ☐ | Edit |
| Jam, Saiva | SJ | sh@gmail.com | | ☐ | ☐ | ☐ | Edit |
| Jones, Franky Smith | FSJ | envyfx@gmail.com | 1/16/11 4:18:32 PM | ☑ | ☐ | ☑ | Edit |
| Kholes, Jennifer | JK | jk@gmail.com | | ☐ | ☐ | ☐ | Edit |
| Killer, Stephanie | SK | sk@gmail.com | 12/6/11 7:07:17 AM | ☐ | ☑ | ☑ | Edit |
| LaBorde, David | DL | dlaborde@gmail.com | | ☐ | ☐ | ☐ | Edit |
| Laos, Franky | FL | fl@gmail.com | | ☑ | ☐ | ☐ | Edit |
| Law, Jaya | JL | jl@gmail.com | | ☑ | ☐ | ☐ | Edit |
| Lee, Saji | SL | ls@gmail.com | | ☑ | ☐ | ☐ | Edit |

Invited Users (Pending Registration)

Search: _____

| E-Mail ▲ | Physician ◇ | Admin ◇ | Invited By ◇ | Expires On ◇ | Edit ◇ | Delete ◇ |
|---|---|---|---|---|---|---|

There are no users to show

Registered Users (Pending Verification)

Search: _____

| E-Mail ▲ | Physician ◇ | Admin ◇ | Invited By ◇ | Expires On ◇ | Edit ◇ | Delete ◇ |
|---|---|---|---|---|---|---|

There are no users to show

FIG. 28

| Patient List | Encounter Query | Admin | | | | | | | Last Login: 16-Dec-2011 07:07:17 AM EST |

Search Encounters

Admittance Date Range: [▦] to [▦]
Procedure Date Range: [▦] to [▦]
Encounter Type: [All ▾]
Facility: [All ▾]
Admitting MD: [Ramen, Sushi ▾]
Disposition Type: [All ▾]
Morbidity: [All ▾]

(Search)

2950

Show [50 ▾] entries

| Facility | Unit | Room | MD | Name | MRN | Age | DOA | Diagnosis | Procedure/Treatment |
|---|---|---|---|---|---|---|---|---|---|
| ISUH | Ectopic | 7160 | SR | Pena, Steph | 14575730 | 43y | 7/31 | | |
| TMH | Ectopic | 3569 | SR | Watts, Manuel | 8230243 | 95y | 4/10 | | |

Showing 1 to 2 of 2 entries

[First | Previous | 1 | Next | Last]

FIG. 29B

| Patient List | Reports | Images | Admin |

Reports

M&M Report
Resident Operative Experience Report
Program Case Log Report

M&M Report

Hospital [Select hospital... ▽]

Date [ 🔲 ] TO [ 🔲 ]

[Print/PDF]

FIG. 30

| PLM - RCM | ⚙ Coder Inbox | ⓘ Support | | | | | | | |
|---|---|---|---|---|---|---|---|---|---|
| All Charges | Nephrology Associates | Neurology Consultants | Dr. Jones | Dr. Hunnicutt | | | | | |
| Show Filters | | | | | | | | | |
| Show [10 ▾] entries | | | | | | ← Previous | Showing 1 to 4 of 4 | Next → | |
| Status | Created ▽ | Physician | Facility | DOS | Patient | DOB | CPT(s) | ICD(s) | Tags |
| New ▾ | 01/23/2015 22:56 | Hunnicutt, B.J. MD | Galaxy Hospital | 01/23/2015 | Kent, Clark (M) | 04/18/1938 | 99223 | 481 | (Insurance Missing) (Hunnicutt Question) |
| Acknowledged ▾ | 01/23/2015 13:38 | Pierce, B. F. MD | Themyscira Hospital | 01/23/2015 | Prince, Diana (F) | 12/04/1941 | 52332 | 592.0 | (Pierce Question) |
| Posted ▾ | 01/23/2015 12:42 | Blake, H. MD | Gotham Hospital | 01/23/2015 | Wayne, Bruce (M) | 05/26/1939 | 99231 | 410 | |
| Denied ▾ | 01/23/2015 09:56 | Potter, S. T. MD | Marvel Hospital | 01/23/2015 | Banner, Robert B. (M) | 05/07/1962 | 99232 | 584.5 | (Needs Precert#) |

FIG. 40

| PLM - RCM | ⌂ Coder Inbox | ⌕ Support | | | | | | | |
|---|---|---|---|---|---|---|---|---|---|
| All Charges | Nephrology Associates | Neurology Consultants | Dr. Jones | Dr. Hunnicutt | | | | | |

Hide Filters

Patient
[Patient name or MRN...]

Status
[All ▾]

Physician
[All ▾]

Practice
[All ▾]

Start Date
[mm/dd/yyyy]

End Date
[mm/dd/yyyy]

[Filter] [Clear Filters]

Show [10 ▾] entries

← Previous | Showing 1 to 4 of 4 | Next →

| Status | Created | Physician | Facility | DOS | Patient | DOB | CPT(s) | ICD(s) | Tags |
|---|---|---|---|---|---|---|---|---|---|
| New ▾ | 01/23/2015 22:56 | Hunnicutt, B.J. MD | Galaxy Hospital | 01/23/2015 | Kent, Clark (M) | 04/18/1938 | 99233 | 481 | Insurance Missing, Hunnicutt Question |
| Acknowledged ▾ | 01/23/2015 13:38 | Pierce, B.F. MD | Themyscira Hospital | 01/23/2015 | Prince, Diana (F) | 12/04/1941 | 52332 | 592.0 | Pierce Question |
| Posted ▾ | 01/23/2015 12:42 | Blake, H. MD | Gotham Hospital | 01/23/2015 | Wayne, Bruce (M) | 05/26/1939 | 99231 | 410 | |
| Denied ▾ | 01/23/2015 09:56 | Potter, S.T. MD | Marvel Hospital | 01/23/2015 | Banner, Robert B. (M) | 05/07/1962 | 99232 | 584.5 | Needs Precert# |

| PLM - RCM | ⌂ Coder Inbox | ⚙ Support | | | | | | |
|---|---|---|---|---|---|---|---|---|
| All Charges | Nephrology Associates | Neurology Consultants | Dr. Hunnicutt | Insurance Missing | | | | |
| Show Filters | | | | | | | | |
| Show 10 ▽ entries | | | | | ← Previous | Showing 1 to 1 of 1 | Next → | |
| Status | Created ▽ | Physician | Facility | DOS | Patient | DOB | CPT®(s) | ICD(s) | Tags |
| Acknowledged ▽ | 01/23/2015 13:38 | Pierce, B.F. MD | Themyscira Hospital | 01/23/2015 | Prince, Diana (F) | 12/04/1941 | 52332 | 592.0 | (Pierce Question) |

FIG. 45

| PLM - RCM | ⌂ Coder Inbox | ⚙ Support | | | | | | |
|---|---|---|---|---|---|---|---|---|
| All Charges | Nephrology Associates | Neurology Consultants | Dr. Hunnicutt | Insurance Missing | | | | |
| Show Filters | | | | | | | | |
| Show 10 ▽ entries | | | | | ← Previous | Showing 1 to 1 of 1 | Next → | |
| New ▽ | 01/23/2015 22:56 | Hunnicutt, B.J. MD | Galaxy Hospital | 01/23/2015 | Kent, Clark (M) | 04/18/1938 | 99233 | 481 | (Insurance Missing) (Hunnicutt Question) |

FIG. 46

| PLM - RCM | ⇦ Coder Inbox | ⌕ Support | | | | | | | |
|---|---|---|---|---|---|---|---|---|---|
| All Charges | Nephrology Associates | Neurology Consultants | Dr. Hunnicutt | Insurance Missing | | | | | |
| Show Filters | | | | | | | | | |
| Show [10 ▽] entries | | | | | ← Previous | Showing 1 to 4 of 4 | Next → | | |
| Status | Created ▽ | Physician | Facility | DOS | Patient | DOB | CPT®(s) | ICD(s) | Tags |
| New ▽ | 01/23/2015 | Hunnicutt, B.J. MD | Galaxy Hospital | 01/23/2015 | Kent, Clark (M) | 04/18/1938 | 99233 | 481 | (Insurance Missing) (Hunnicut Question) |
| Acknowledged | | | | | | | | | |
| Awaiting Physician Charting | | Pierce, B.F. MD | Themyscira Hospital | 01/23/2015 | Prince, Diana (F) | 12/04/1941 | 52332 | 592.0 | (Pierce Question) |
| Awaiting Pre Certification | | | | | | | | | |
| Bad Debt | | Blake, H. MD | Gotham Hospital | 01/23/2015 | Wayne, Bruce (M) | 05/26/1939 | 99231 | 410 | |
| Denied | | | | | | | | | |
| Posted | | Potter, S.T. MD | Marvel Hospital | 01/23/2015 | Banner, Robert B. (M) | 05/07/1962 | 99232 | 584.5 | (Needs Precert#) |
| 09:56 | | | | | | | | | |

| PLM - RCM | ⬥ Coder Inbox | ⬥ Support | | | | | | | |
|---|---|---|---|---|---|---|---|---|---|
| All Charges | Nephrology Associates | Neurology Consultants | Dr. Hunnicutt | Insurance Missing | | | | | |
| Show Filters | | | | | | | | | |
| Show [10 ▾] entries | | | | | | ← Previous | Showing 1 to 4 of 4 | Next → | |
| Status | Created ▾ | Physician | Facility | DOS | Patient | DOB | CPT®(s) | ICD(s) | Tags |
| New ▾ | 01/23/2015 22:56 | Hunnicutt, B.J. MD | Galaxy Hospital | 01/23/2015 | Kent, Clark (M) | 04/18/1938 | 99233 | 481 | Insurance Missing, Hunnicut Question |
| Acknowledged ▾ | 01/23/2015 13:38 | Pierce, B.F. MD | Themyscira Hospital | 01/23/2015 | Prince, Diana (F) | 12/04/1941 | 52332 | 592.0 | Pierce Question |
| Posted ▾ | 01/23/2015 12:42 | Blake, H. MD | Gotham Hospital | 01/23/2015 | Wayne, Bruce (M) | 05/26/1939 | 99231 | 410 | |
| Denied ▾ | 01/23/2015 09:56 | Potter, S.T. MD | Marvel Hospital | 01/23/2015 | Banner, Robert B. (M) | 05/07/1962 | 99232 | 584.5 | Needs Precert# |

SYSTEM, CLIENT DEVICE, SERVER AND METHOD FOR PROVIDING A CROSS-FACILITY PATIENT DATA MANAGEMENT AND REPORTING PLATFORM

CROSS-REFERENCE TO RELATED APPLICATIONS

The present application is a continuation-in-part application of U.S. patent application Ser. No. 13/724,163 filed on Dec. 21, 2012, which claims the benefit of U.S. Provisional Patent Application No. 61/579,956 filed on Dec. 23, 2011.

TECHNICAL FIELD

The technical filed generally relates to a system including one or more client devices and servers for securely storing and accessing patient data and, more specifically to such a system for providing a means for storing and accessing patient data across multiple points of care locations utilizing a centralized repository and web enabled technologies.

BACKGROUND

Conventionally, a medical service provider such as a physician stores information regarding a patient (patient data) at a facility level. When another medical service provider at a different facility provides a medical service to the same patient, the patient data associated with this care episode will also be stored at the different facility. This silo approach to storing patient data can limit the ability of medical service providers that provide services across one or more facilities to access the patient data. In some cases, these limitations are present even among different medical service providers in a same facility.

PRIOR ART

U.S. Pat. No. 7,353,238 for an Apparatus and methods for determining and processing medical outcomes, Richard E. Gliklich, Boston, Mass.

U.S. Publication number: US 2011/0153351 A for a Collaborative medical imaging web application, Gregory Vesper et al U.S. Publication number: US 2011/0110568 A1 for a Web enabled medical image repository, Gregory Vesper et al

SUMMARY

Medical service providers are faced with challenges that result from the silo approach of storing patient data. For example, physicians cannot obtain rapid access to some of the information in order to provide the best care for their patients. Further, this information is not readily available in one interface. The providers have to instead access the records physically (for those facilities on paper based records), electronically (if the facilities at which they are providing services are on electronic medical records, for example), or by using manual workarounds such as manually writing information on paper. These problems are exacerbated by the fact that many physicians see patients across multiple facilities having different data capture and clinical information/documentation solutions (paper, electronic medical record systems, etc.). Thus, accessing the information needed from each facility is a distinct process at each facility. Even those facilities which store medical records electronically have systems that do not communicate with similar systems at unaffiliated facilities and often the IT system in the physician or other provider's outpatient office. Moreover, remote access to the information systems at multiple unaffiliated facilities via one interface is not commonplace in the current prevailing paradigm.

In view of the above problems, as well as other concerns, the present disclosure concerns a system for providing a patient data management platform accessible via different facilities (cross-facility) which will be referred to as a patient list manager. In the system, one or more client devices and server devices provide a platform in which patient data can be securely accessed and modified across multiple points of care.

According to one aspect, the patient list manager client device includes a transceiver, a controller coupled to the transceiver, and a memory including instructions for configuring the controller. The transceiver communicates with a server (patient list manager device) via a connection to a network such as a LAN, the Internet, or cellular network.

The controller is configured to generate a resource request including an authentication credential to be sent to the patient list manager device, decrypt encrypted data received from the patient list manager device in response to the resource request, and generate a top level display based upon the decrypted data.

The top level display can include a patient list graphical interface, an administrative level graphical interface and an encounter query graphical interface in accordance with the user credential.

A patient list display is generated when the patient list graphical interface is selected. The patient list display includes one or more graphical interface filters, an add (or edit) patient graphical interface, and a remove patients graphical interface.

The patient list manager device includes a transceiver configured to receive a resource request from a remote patient list manager client device, the resource request including verification credentials issued from a certification authority and a user name; a controller operatively coupled to the transceiver; and one or more memory sources operatively coupled to the controller. The one or more memory sources can include a patient list database and instructions for configuring the controller.

The instructions configure the controller to verify the resource request. Particularly, the controller confirms that the certification authority is one of a number of predetermined trusted certification authorities. Once confirmed, a secure communication session between the patient list manager device and the patient list manager client device is established. The controller can determine data in the patient list database that is associated with a user name associated with the resource authentication request, and encrypt at least a portion of the determined data in accordance with a predetermined encryption protocol to be sent to the patient list manager client device during the secure communication session by the transceiver. The data may be sent over Secure Sockets Layer (SSL) or Transport Layer Security (TLS) or other similar cryptographic protocols which provide secure communications over a computer network. The data packets traveling over SSL, TLS, or other similar cryptographic protocols may or may not also be encrypted independent of SSL, TLS, or other similar protocols.

The patient list database includes a plurality of patient identifications and patient attributes associated with each of the patient identifications. The patient attributes include a facility, an encounter type for a care episode, one or more diagnoses for the care episode, one or more disposition types for the care episode, one or more procedure types, one or more physicians or other medical service provider names and roles of the physicians or other medical service providers, and a morbidity indication such as a tag.

The patient list manager can be implemented by a virtual machine on the server interacting with a database on the same virtual machine or a different virtual machine. The client device can be implemented by a computing device including a web browser or a native application running on the client device. The client devices communicate with the patient list manager device(s) via one or any combination of the following means: a REST-like application programming interface (API), a Representational State Transfer (REST)-ful API, via Remote Procedure Calls (RPC) over Hypertext Transport Protocol (HTTP), and/or any other client-server communications protocols for networked applications. The patient list manager can be a single install (i.e. installed in a hospital data center and used by the various clinical departments/physician groups—medicine, general surgery, rehab medicine, etc. but each only sees their own data) or a multi-tenant installation. For example, the patient list manager can be hosted in a third party data center and multiple hospitals and physician groups utilize the installation but do not see each other's data. The data can be replicated across multiple database servers (i.e. data mirroring) for redundancy and an implementation may have multiple machines running the patient list manager device with a load balancer (and a fire wall) in front of the backend application machines (i.e. servers or virtual machines) to distribute the requests equitably so the system can handle more demand/traffic and ensure quality user experience (speed, etc.).

Other modules implemented by either the same or different virtual machines can analyze and use the patient data in the patient list database or further annotate additional information on patient care episodes in the patient list manager device database. These modules may allow a machine (i.e. a device with integrated sensors or a server with business logic enabling it to respond to particular events) to annotate in response to a plurality of events or allow end users to annotate (via patient list client devices) the care episodes on the patient list with additional data relevant to the particular module's purpose.

One example module is a charge capture and revenue cycle management module which provides functionality that is used to manage the process of obtaining patient billing information, details about services rendered, and payment for services rendered. Obtaining payment includes, but is not limited to, preparing and sending medical claims to medical insurance companies, workers compensation insurers, third party adjudicators, and/or the employers of patients (and managing the process of obtaining final payment). The patient list manager client devices enable end users to easily annotate the patient list manager records of patients being cared for (patients on the patient list). As a result, the patient list manager devices allow for convenient and secure assembly (collection and submission) of pertinent medical billing data and secure real-time collaboration with other stakeholders involved with managing the revenue cycle (i.e. medical coders, medical billers, revenue cycle managers, practice administrators, etc.) and obtaining the requisite data needed to accurately bill for medical services provided to patients across one or multiple facilities. Data collected by such modules may be of a variety of types and may come from a plurality of sources, including, but not limited to, details about the patient's insurance, employer or other payer information either from the patient, the medical facility, or another third party, data detailing and documenting (memorializing) what and when specific medical services were provided to a patient; this data may be collected actively, for example by a medical service provider who provides information or billing codes or other individuals reviewing documentation and other artifacts from an episode of care between a patient and a medical service provider. This may also occur passively, for example by a machine operating a patient list manager client device that generates annotations in response to certain external events, such as an Health Level 7 (HL7) message or sensor data about the proximity and duration of proximity of one or more human or other non-human physical assets. Data about an episode of care between a medical service provider and a patient may include, but is not limited to billing codes (i.e. diagnosis codes, evaluation and management codes, modifier codes, and/or procedure codes), dates of service, locations of service, account numbers, visit numbers, medical record or unit numbers, enterprise master patient index numbers, free text information, provider charting, narratives, images, video, audio, short message service (SMS) data, indoor positioning system data, global positioning data (GPS), cellular tower data, wireless access point data, radio-frequency identification (RFID) data, near field communications data, or other sensor data from a mobile or stationary device.

Another example module is a diagnostic imaging module for uploading and viewing imaging studies; and reporting modules for generating various reports.

The patient list manager modules and applications running on server and client devices can be configured as a suite of microservices and applications, each with the responsibility for one or multiple related tasks or functions. The patient list manager device can be deployed utilizing one or a plurality of the following strategies: i) running multiple instances of an the patient list manager devices with a load balancer to distribute inbound requests equitably, ii) running the patient list manager and its modules as independent microservices, each focused on a particular use case or task or each focused on all tasks related to a particular resource or entity, iii) sharing or partitioning data across a set of patient list manager database servers separating or organizing the data based on a characteristic, property or attribute of the data and utilizing a component to route requests to the correct server. The patient list manager provides single sign-on functionality for not only the patient list manager but all the modules as well.

BRIEF DESCRIPTION OF THE DRAWINGS

FIG. 1D is a block diagram illustrating exemplary portions of the patient list manager client device according to an exemplary embodiment.

FIG. 1E is a block diagram illustrating exemplary portions of the system according to an exemplary embodiment.

FIG. 5 is an exemplary screen shot of a top level display which includes a patient list display.

FIG. 6 is an exemplary screen shot of a patient list display showing close up of patient list manager current encounter filters.

FIG. 7 is an exemplary screen shot of a patient list display showing close up of patient list manager current encounter hospital filter pull down menu.

FIG. 8 is an exemplary screen shot of a patient list display showing close up of patient list manager current encounter physician/physician group filter pull down menu.

FIG. 9B is an exemplary screen shot of a patient list display highlighting the add patient graphical button.

FIG. 10 is an exemplary screen shot of a patient list add (or edit) patient display.

FIG. 11 is an exemplary screen shot of a patient list add (or edit) patient display when the categorical encounter type pull down menu is selected.

FIG. 12 is an exemplary screen shot of a patient list add (or edit) patient display when the categorical diagnosis type pull down menu is selected.

FIG. 13 is an exemplary screen shot of a patient list add (or edit) patient display when add procedure functionality is selected.

FIG. 14 is an exemplary screen shot of a patient list display highlighting the portable document format (PDF) patient list generation button.

FIG. 15 is an illustration of an exemplary PDF patient list generated by the patient list manager.

FIG. 16 is an exemplary screen shot of a patient list display highlighting the remove patient button.

FIG. 17 is an exemplary screen shot of a patient list remove display.

FIG. 18 is an exemplary screen shot of a patient list remove display showing disposition type pull down with categorical options user can choose among.

FIG. 19 is an exemplary screen shot of a patient list remove display showing functionality that enables a user to tag a particular care episode as a morbidity and provide additional detail.

FIG. 20A is an exemplary screen shot of the administrative panel display of the patient list manager showing administrative panel audit log functionality and viewing interface.

FIG. 21 is an exemplary screen shot showing administrative panel area where diagnosis pull down list in the patient list manager is edited, modified, or customized.

FIG. 22 is an exemplary screen shot showing administrative panel area where disposition type pull down list in the patient list manager is edited, modified, or customized.

FIG. 23 is an exemplary screen shot showing administrative panel area where encounter type pull down list in the patient list manager is edited, modified, or customized.

FIG. 24 is an exemplary screen shot showing administrative panel area where facility name (i.e. hospital) pull down list in the patient list manager is edited, modified, or customized.

FIG. 25 is an exemplary screen shot showing administrative panel area where physician grouping functionality (filter setting allowing patient list to be filtered by a subspecialty group, for example, within a larger physician group practice) is managed, edited, modified, and customized.

FIG. 26 is an exemplary screen shot showing administrative panel area where procedure pull down list in the patient list manager is edited, modified, or customized.

FIG. 27 is an exemplary screen shot showing administrative panel area where the unit type/name pull down list (which drives patient list grouping in the graphical user interface and permits patient list to fit within rounding workflow of physician end users) in the patient list manager is edited, modified, or customized.

FIG. 28 is an exemplary screen shot showing administrative panel area where the system user access and new user account creation and validation is managed by the local site/practice administrator.

FIG. 29B is an exemplary screen shot showing the basic query engine interface with customizable criteria.

FIG. 30 is an exemplary screen shot illustrating the report builder module interface example showing morbidity and mortality report generation interface.

FIG. 40 is an exemplary screen shot of the Revenue Cycle and Coding Operations Manager graphical interface list display.

FIG. 41 is an exemplary screen shot of the Revenue Cycle and Coding Operations Manager graphical interface list display showing the filters.

FIGS. 42-44 are exemplary screen shots of the Revenue Cycle and Coding Operations Manager graphical interface list displays when the pull down graphical interface filters are selected.

FIGS. 45-46 are exemplary screen shots of the Revenue Cycle and Coding Operations Manager graphical interface list displays when list has been filtered.

FIG. 47 is an exemplary screen shot of the Revenue Cycle and Coding Operations Manager graphical interface list display when a status update pull down tab is selected.

FIG. 48 is an exemplary screen shot of the Revenue Cycle and Coding Operations Manager graphical interface list display when the filter tags pull down graphical interface is selected.

FIG. 49 is an exemplary screen shot of the Revenue Cycle and Coding Operations Manager graphical interface list displays showing a custom tag being added.

FIG. 50 is an exemplary screen shot of the Revenue Cycle and Coding Operations Manager graphical interface list display when a dialog box is generated.

DETAILED DESCRIPTION OF PREFERRED EMBODIMENTS

In overview, the present disclosure concerns a system for providing a patient data management and reporting platform (referred to here as a patient list manager). In the system, one or more client devices and servers provide secure storage and access of patient data across different facilities.

The instant disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

It is further understood that the use of relational terms such as first and second, and the like, if any, are used solely to distinguish one from another entity, item, or action without necessarily requiring or implying any actual such relationship or order between such entities, items or actions. It is noted that some embodiments may include a plurality of controllers/processes or steps, which can be performed in any order, unless expressly and necessarily limited to a particular order; i.e., processes or steps that are not so limited may be performed in any order.

Reference will now be made in detail to the accompanying drawings. Wherever possible, the same reference numbers will be used throughout the drawings to refer to the same or like parts.

Figure 1A:
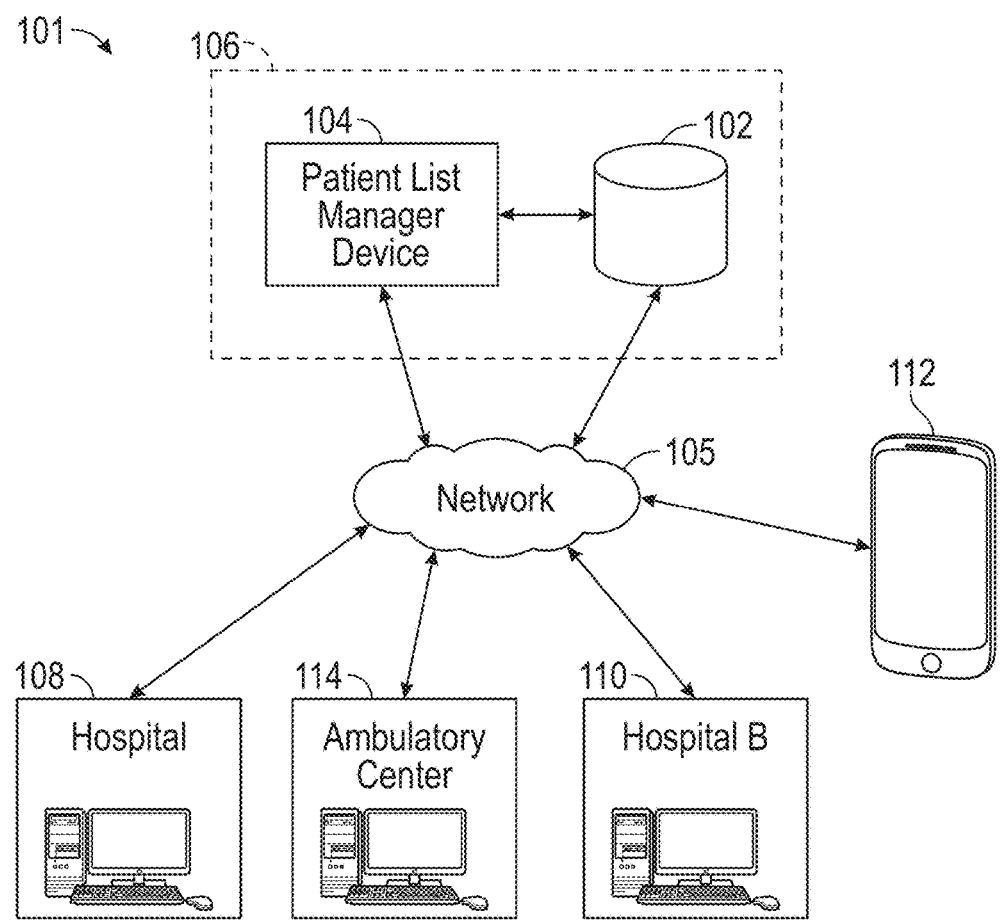
FIG. 1A illustrates an exemplary environment of different facilities in which the patient list manager according to exemplary embodiments can be implemented.

Referring to FIG. 1A, a simplified and representative exemplary environment in which the system for providing a cross facility patient list manager can be implemented will be discussed and described. The environment includes three facilities: a first hospital 108, a second hospital 110, an ambulatory center (outpatient facility, such as a physician office or ambulatory surgery or procedure center) 114, and a smartphone 112, each of which is connected to a network 105 such as a LAN, the Internet, or a cellular network. One or more servers represented generally by 106 provide a patient list manager device 104 and a patient list database 102 which is also connected to the network 105. The connection to the network 105 can be a direct connection such as a wired or wireless connection or can be an indirect connection such as a connection through the Internet, local area network, wide area network, communication network, etc. Further, although the servers were shown merely by dotted box 106, those of skill in the art should appreciate that server 106 can represent entities necessary for providing cloud computing such as infrastructure and services providers.

The patient list manager is a solution that creates value for physicians and other providers that provide services across the multiple often times un-affiliated facilities 108, 110, 114 in addition to possibly seeing patients in their offices (not shown). The patient list manager helps address the issues resulting from gaps in cross-facility data access and the current inability of physicians and other providers to visualize cross-facility data in one interface from the physician or other providers prospective. Physicians and other providers, or groups of such individuals, use the patient list manager, a web-based, cloud hosted, point of care solution accessible via any web-enabled device with an Internet connection such as the smartphone 112 or a subscriber device at, for example, one of facilities 108, 110, 114. The subscriber device and the smartphone can be referred to generally as client devices here as each obtains resources from the servers 106. At each point of care in which the physician or other provider renders services, they login to a website associated with the patient list manager via the client device or access a client specific application and view, abstract and capture structured data about each care episode via the client device (FIGS. 9B-13). They or other authorized members of their practice can then access the information captured in real time and/or near real time anytime, anywhere and utilize it to better care for their patients and improve the efficiency of their practice's operations. The client devices and servers of the system will be discussed in detail.

Figure 1B:
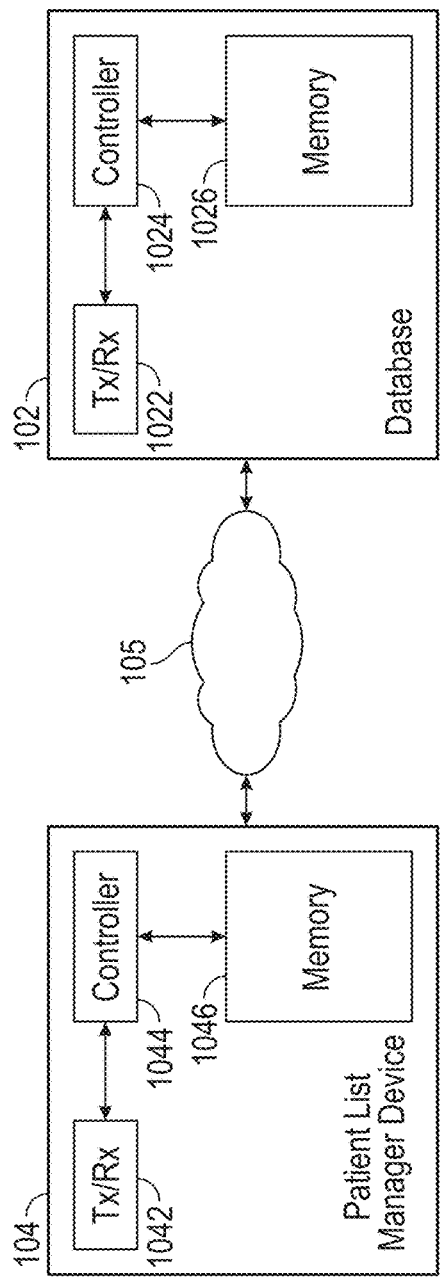
FIGS. 1B-1C are block diagrams illustrating exemplary portions of the patient list manager device according to exemplary embodiments.

As mentioned above, one or more servers 106 provide patient list manager device 104 and the patient list database 102. As shown in FIG. 1B, the patient list manager device 104 includes a transceiver 1042, a controller 1044 and memory 1046. The patient list database 102 also includes a transceiver 1022, a controller 1024 and a memory 1026. The transceivers 1022, 1042 are configured to communicate via a connection to the network 105. For the patient list manager device 104, the transceiver receives resource requests such as, for example, http requests, via the network 105 from a client device. The resource request can include verification credentials such as a token issued from a certification authority and a user name.

Figure 1C:
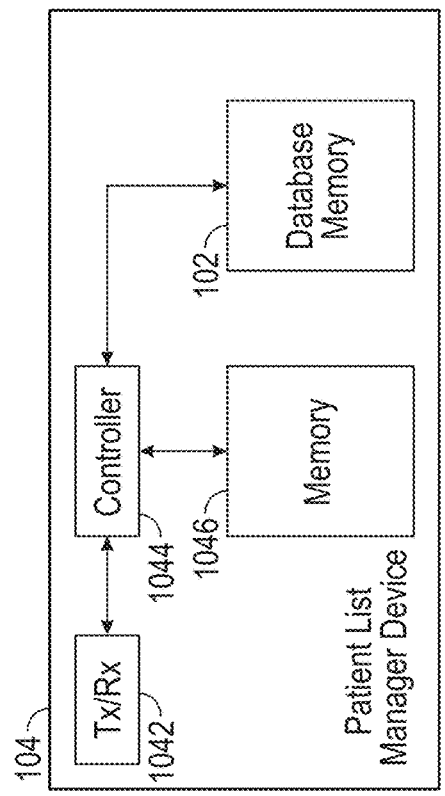

The memory 1026, 1046 can be one or a combination of a variety of types of memory such as random access memory (RAM), read only memory (ROM), flash memory, dynamic RAM (DRAM) or the like. Alternatively, as shown in FIG. 1C, the patient list database 102 can be a portion of the patient list device 104. The memory 1026, 1046 includes instructions for the controllers 1024, 1044 to execute processes for providing the patient list manager.

The patient list database stores a plurality of patient identifications and patient attributes associated with each of the patient identifications. The patient attributes include a facility, an encounter type for a care episode, diagnosis for the care episode, a disposition type for the care episode, a procedure type, the name of one or more physicians and/or other medical providers and their role, and a morbidity indication such as a tag. The patient list database 102 also stores a plurality of user names and associations of each of the user names with predetermined patient identifications.

It should be noted that in FIGS. 1B-1C, one server was shown merely for ease of illustration. However, as shown in FIG. 1E, the system for providing the patient list manager can include a plurality of servers and databases 170 connected to the network 105 via a load balancer 165. The patient list manager can be implemented by performing X, Y and Z axis scaling of the hardware and software. Particularly, multiple virtual machine instances (VMs) can be running the patient list manager applications behind the load balancer 165 on the different servers (X-axis), the servers can perform a functional decomposition to break up applications into small services (Y-axis), and each server (running the identical app) can be responsible for a subset of the data (sharding the database) broken up by something that logically makes sense for the business (i.e. patient last name, type of customer, etc.) with a component for routing (Z-axis).

Returning to the patient list manager device 104, the memory 1046 includes instructions for configuring the controller 1044. For example, the controller 1044 and memory 1046 can be an application specific integrated circuit (ASIC) or the instructions can be software. The instructions configure the controller 104 to verify a resource request received by the transceiver 1042. Once verified, a secure communication session is established between the patient list manager device 104 and the patient list manager client device. The controller 1044 determines data in the patient list database 102 that is associated with a user name associated with the resource request. This data is obtained from the patient list database 102, and a predetermined portion of it is encrypted in accordance with a predetermined encryption protocol. The transceiver 1042 sends the encrypted data to the patient list manager client device during the secure communication session possibly over SSL or TLS and the patient list manager client device decrypts the data and presents it in the graphical user interface to the end user.

Figure 3A:
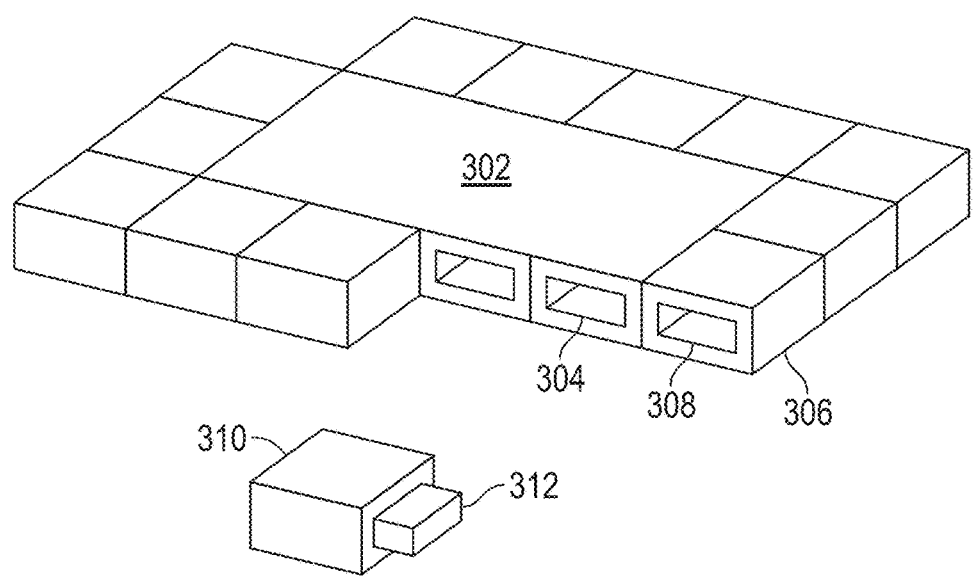
FIG. 3A is an illustration of the modular design of the patient list manager.
Figure 3B:
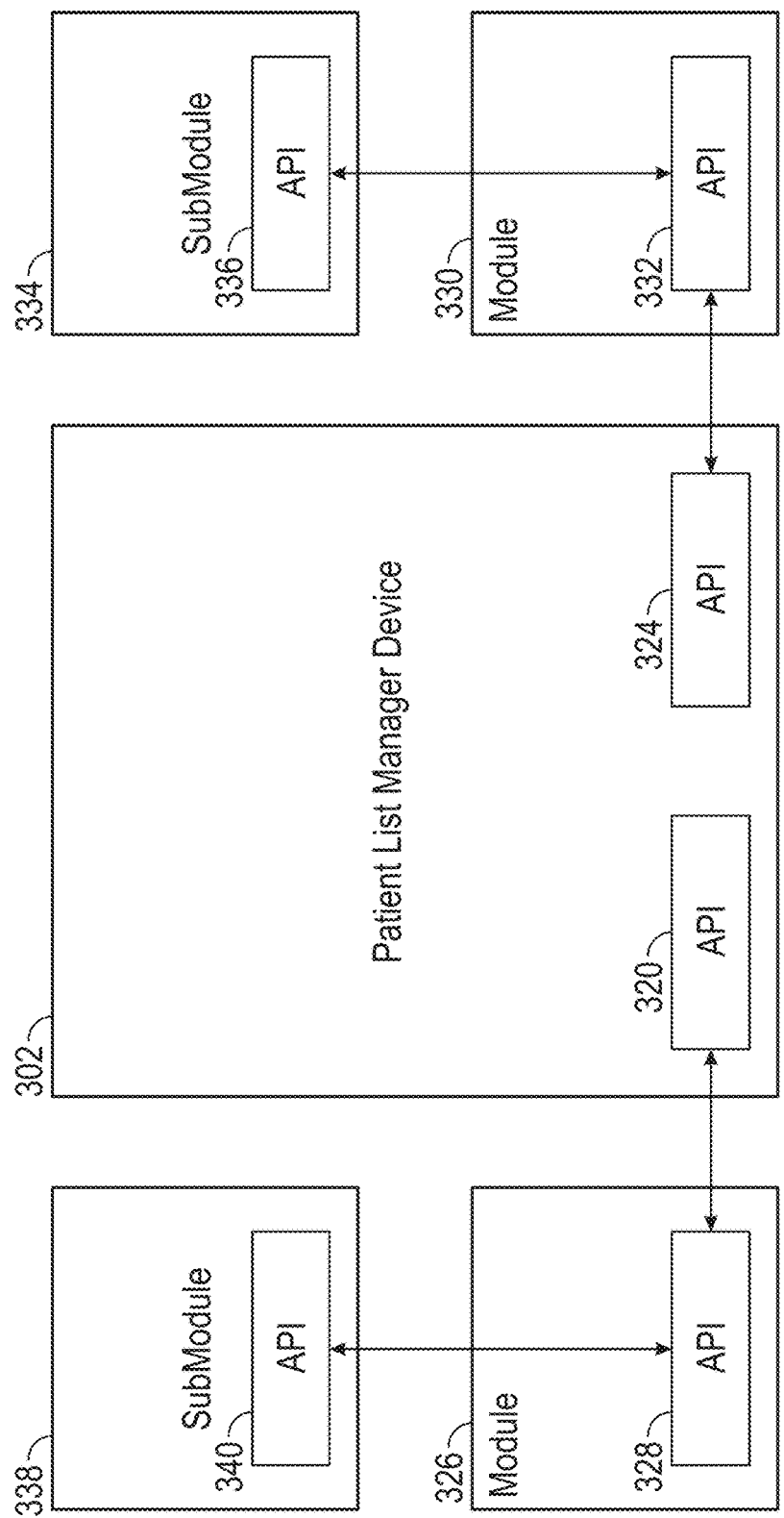
FIGS. 3B-3C are block diagrams illustrating the patient list manager device connected to plural modules and submodules according to various exemplary embodiments.

Referring to FIG. 3A, the modular configuration of the patient list manager will be introduced. The patient list manager device 302 is a base module for end users. However, several additional modules and even sub-modules adding additional functions for the end users can be added. Each module 310 or sub-module includes a connection interface 312 for connecting with a connection interface 304 of the patient list manager device 302 or a connection interface 308 of a different module 306 or sub-module. As shown in FIG. 3B, these interfaces may be implemented by an application program interface (API) at the patient list manager device 302 and each of the modules and sub-modules. Each of the modules and sub-modules can be virtual machines on which the application(s) sit on a webserver which may interact with a database on the same virtual machine or a different machine. Further, each module can interface with the patient list manager device 302 via a network such as the Internet. In one example shown in FIG. 3C, exemplary modules such as the diagnostic image manager device 358 and the revenue cycle management device 365 communicate with the patient list manager device 350 via the network 105. These modules can connect to the patient list manager device 302 to leverage the patient data in the patient list database 102.

Referring to FIG. 1D, portions of an exemplary client device 150 for accessing patient data from the patient list manager (referred to herein as a patient list manager client device) will be discussed. The client device 150 includes a transceiver 152 for communicating with the patient list manager device via the connection to the network, a controller 154 for executing instructions stored in a memory 156, a display 158 for providing a user interface for the use of the client device 150 and a bus 160. Although not shown, those of skill in the art will appreciate that the client device 150 may also include user input means such as a keyboard, device sensors, device peripherals, and/or the display 158 may be a touch display.

Figure 2:
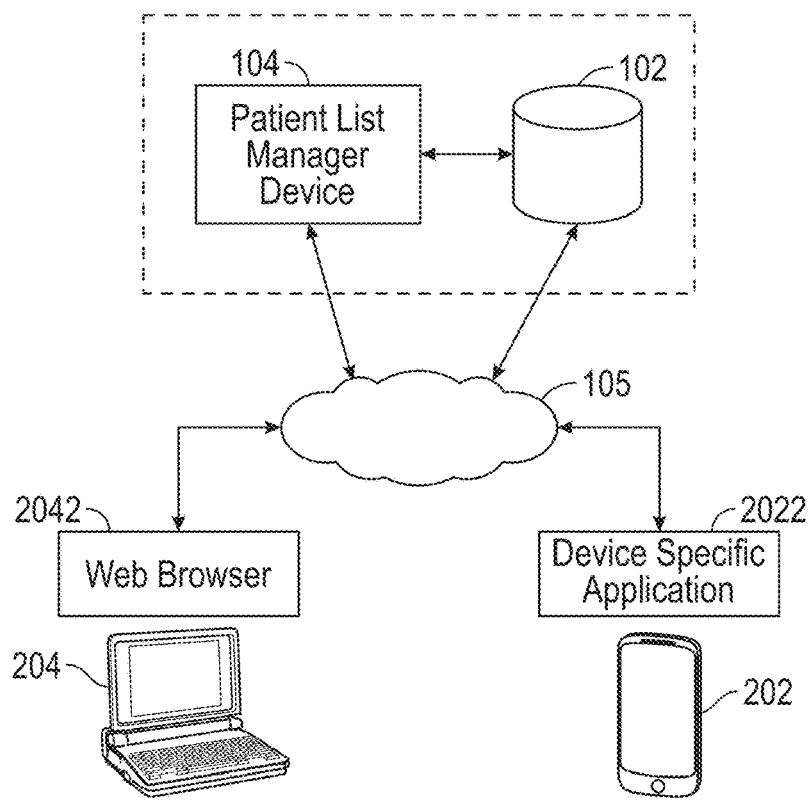
FIG. 2 illustrates an exemplary environment in which the system can be employed.

As shown in FIG. 2, the instructions for configuring the client device can be implemented by, a web browser 2042 which is executing code received via a connection to the network 105 as well as code stored locally on a client device 204 and/or a device specific application 2022 stored locally at the client device 202. For example, the client device can utilize a REST-like, REST-ful, and/or RPC based API for consuming services from a virtual machine on the server as is the file manager device. In either case (or a combination of both), the controller 154 is configured to generate a login screen on the display (158) associated with the patient list manager client device as discussed below.

Figure 4A:
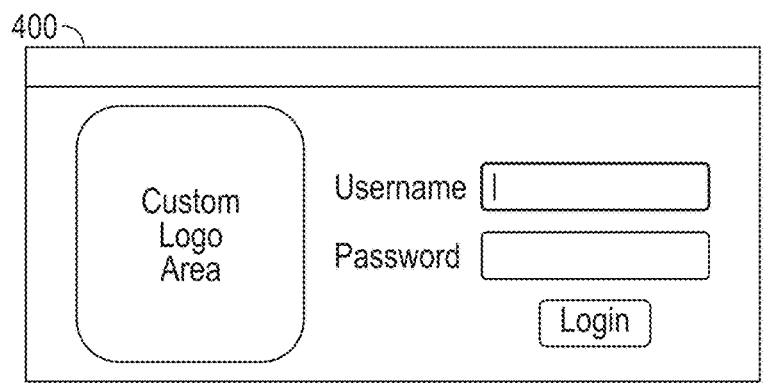
FIG. 4A is an exemplary screen shot of a login screen at the client device.
Figure 4B:
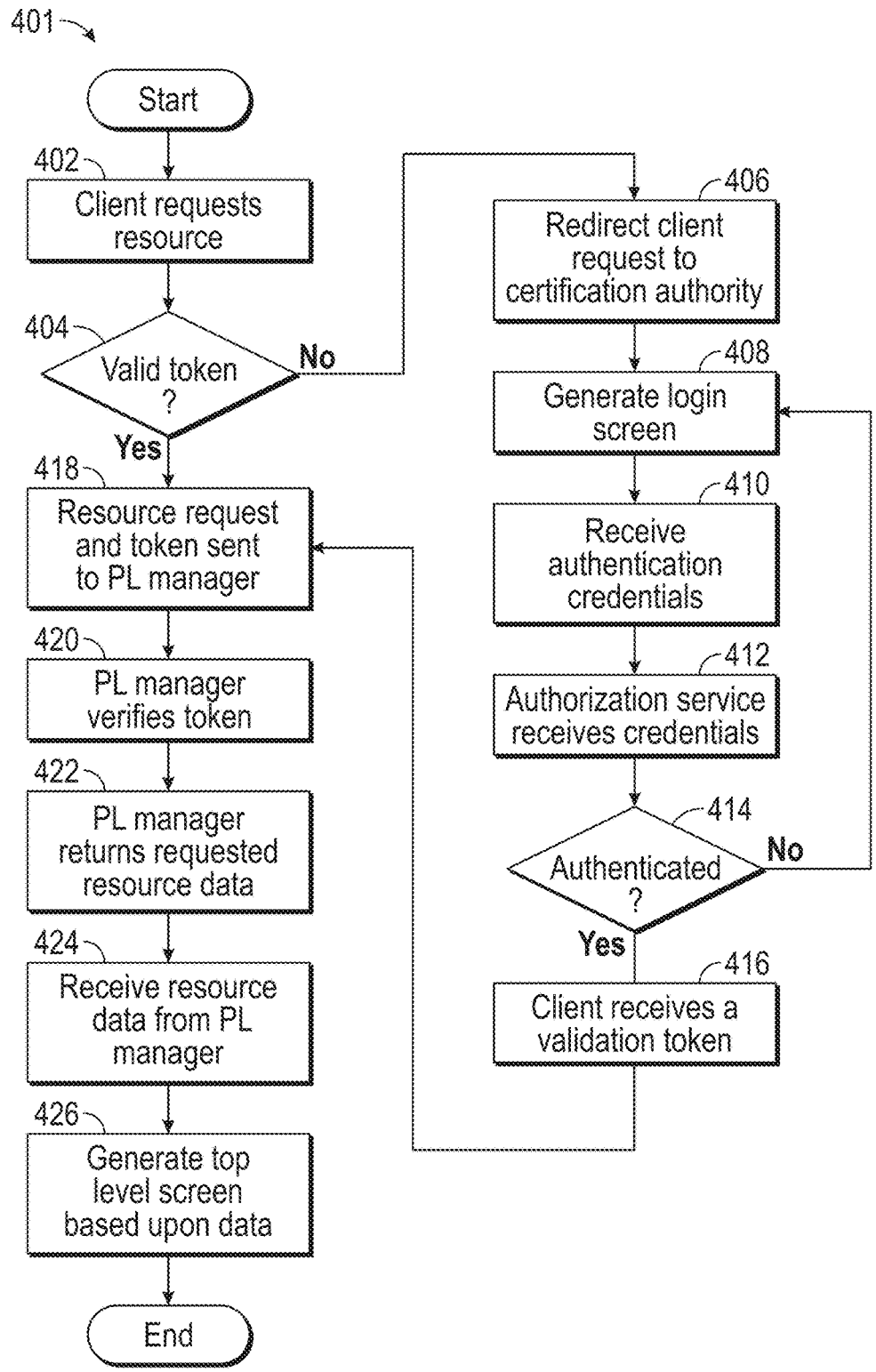
FIG. 4B is a flow diagram of exemplary methodology for securely authenticating a patient list manager client device and generating a top level display.

Referring to the flow diagram of FIG. 4B, an exemplary methodology or routine executed by the patient list manager device and the client device for securely authenticating the client device and generating a top level display on the client device will be discussed. In FIG. 4B, the client device is referred to as client and the patient list manager device is referred to as PL manager. At 402, the client device requests resources from the PL manager. For example, a user of the client device visits a particular website for accessing the PL manager. At 404, an entity such as the PL manager or a certification authority determines if the client device has a valid token (access or refresh token). If the client device does not have a valid token (NO at 404), the resource request is redirected to the certification authority (step 406). If the client device does have a valid token (YES at 404), the process proceeds to 418 discussed below.

Figure 33:
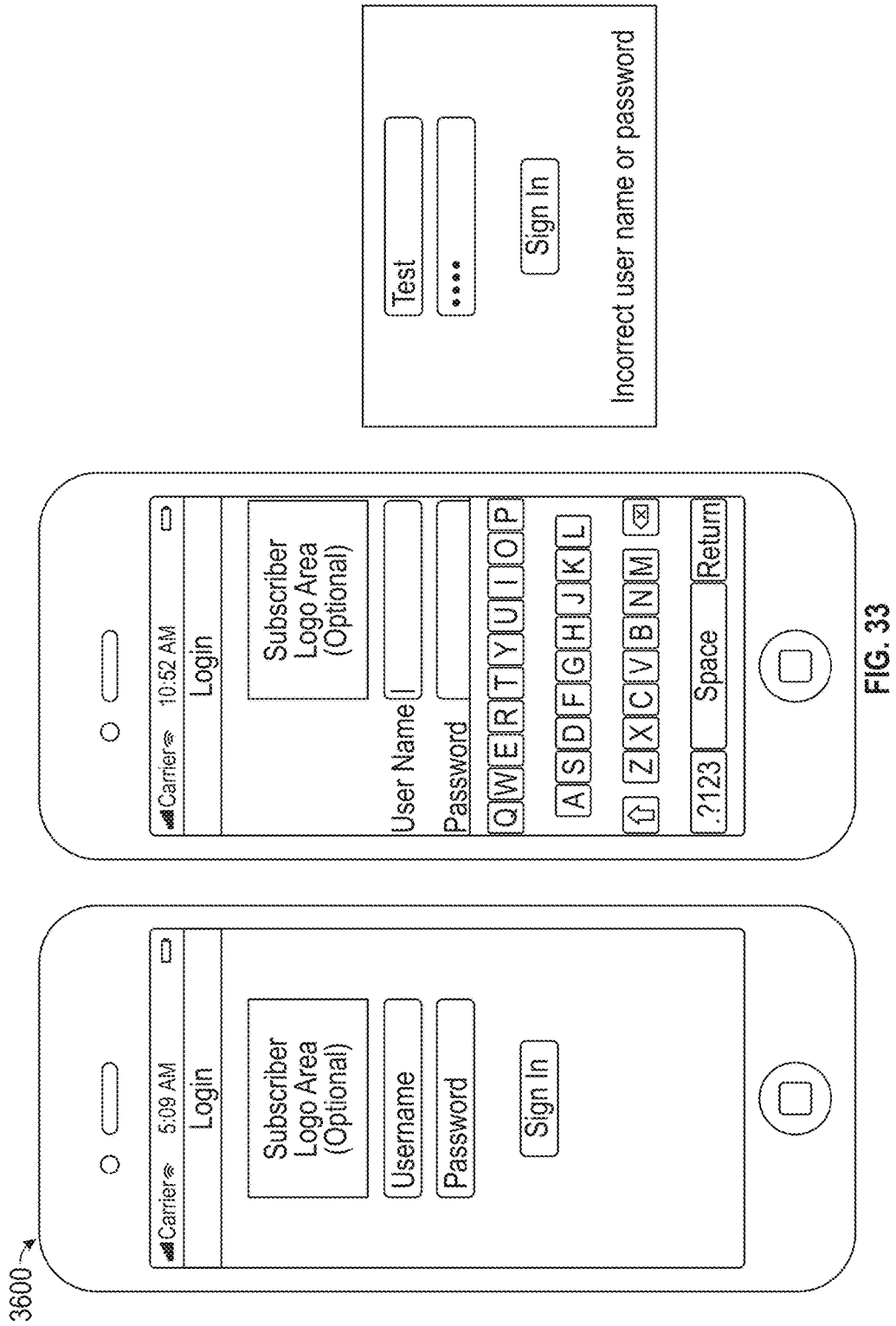
FIG. 33 is a screen shot of an exemplary login screen for a mobile device.
Figure 34:
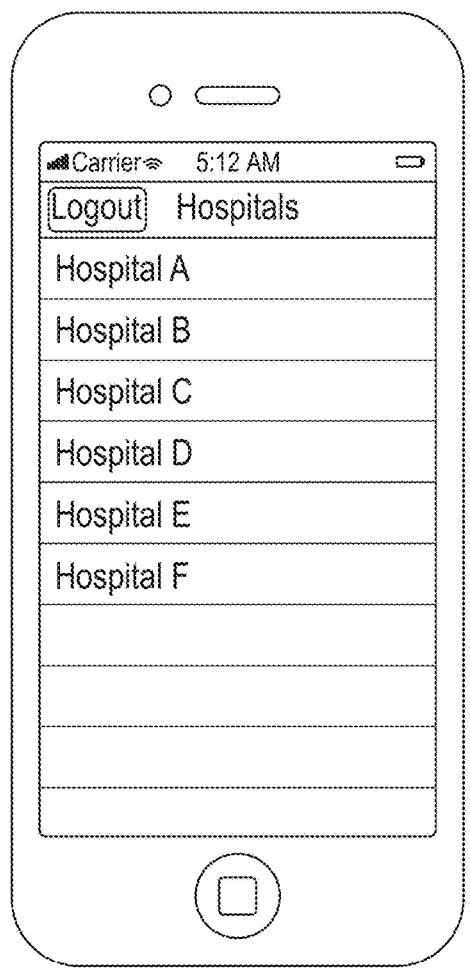
FIG. 34 is a screen shot of the patient list display on the mobile device when the hospital filter is used to filter patient list by hospital.
Figure 35:
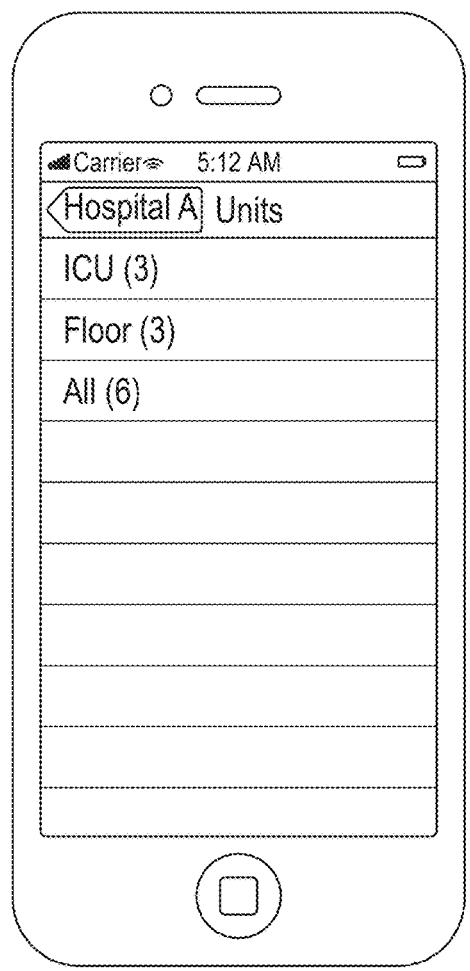
FIG. 35 is a screen shot of the patient list display on the mobile device when the unit filter is used to filter patient list by hospital unit.
Figure 36:
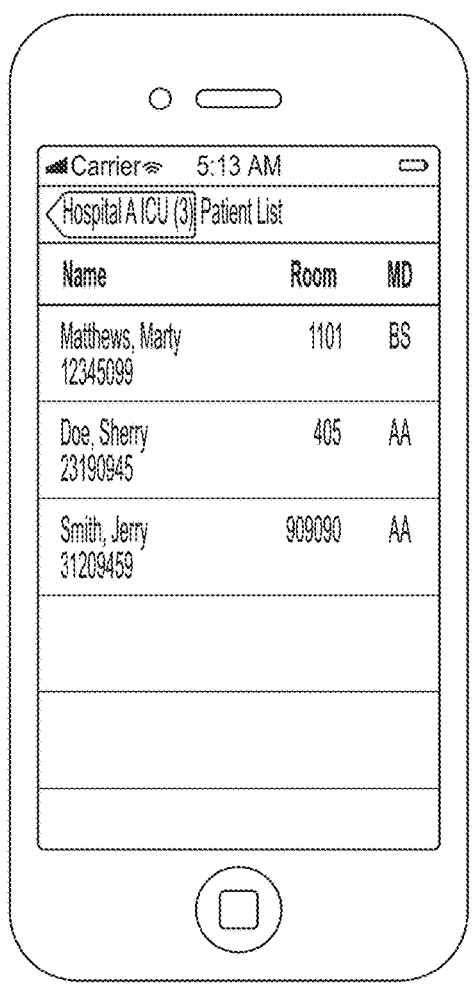
FIG. 36 is a screen shot of the patient list display on the mobile device.
Figure 37:
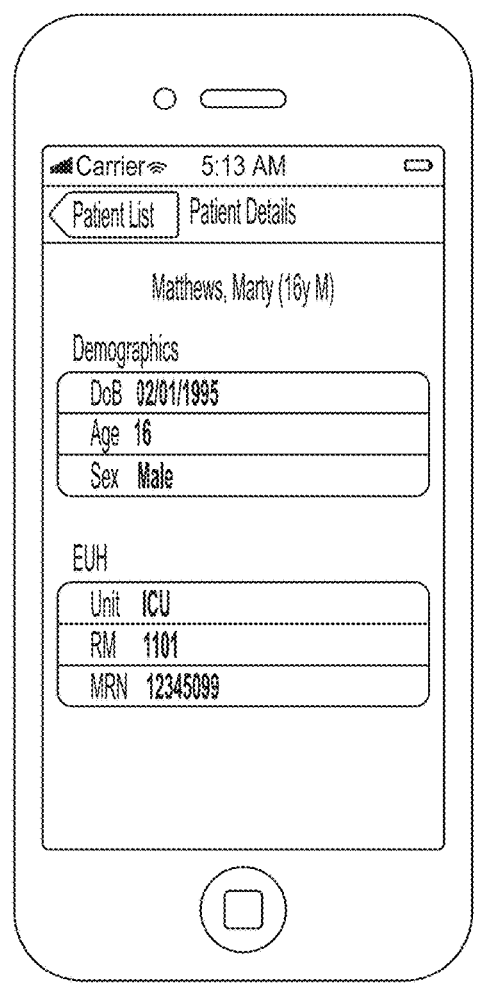
FIG. 37 is a screen shot of the patient list display on the mobile device showing the patient detail screen.

At 408, the client device generates a login screen by executing instructions local to the client device, code received via the Internet, or by merely visiting a website hosted by the patient list manager device or the certificate authority. Exemplary login screens are shown in FIGS. 4A and 33. At 410, the user can enter authentication credentials into the login screen via a user interface at the client device. The transceiver of the client device sends the user credentials to the certificate authority which are received at 412.

At 414, the certification authority determines if the user credentials can be authenticated. If the user credentials can be authenticated (YES at 414), at 416 the client device receives authentication credentials such as a token issued by the certification authority. At 418, the client device generates a resource request including an authentication credential (the token) and a user name. The transceiver of the client device sends the resource request to the PL manager. If the user credentials cannot be authenticated (NO at 414), the client device is returned to the login screen. Although not shown here, the client device can be limited to a certain number of login attempts within a certain time period.

At 420, the PL manager verifies the token. For example, the PL manager confirms that the certification authority that issued the token in the resource request is one of a number of predetermined trusted certification authorities. Although not shown here, if the PL manager cannot verify the token, the client device can once again be returned to 406.

At 422, the PL manager determines the patient data in the patient list database that is associated with the user name in the resource request. For example, the PL manager can retrieve patient data that is associated with the user name in the patient list database. The PL manager encrypts the retrieved patient data according to an encryption protocol such as, for example, HMACsha256 secret key encryption and sends the encrypted data to the client device over SSL or TLS.

At 424, the client device receives the encrypted data from the PL manager in response to the resource request and decrypts the encrypted data according to the encryption protocol. At 426, the client device generates a top level display based upon the decrypted data. The top level display includes a plurality of graphical interfaces for being manipulated by the user.

Figure 5:
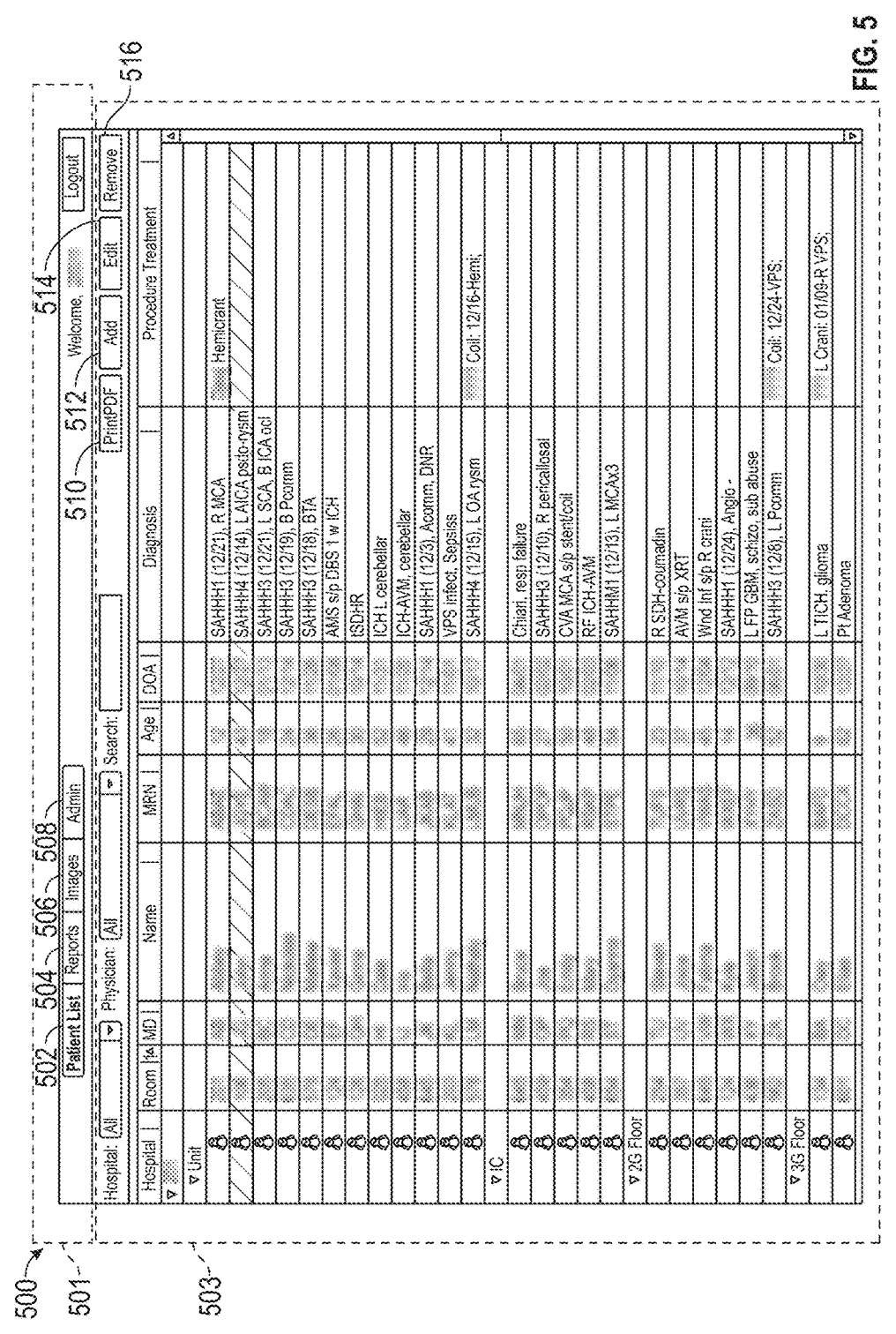
Figure 20B:
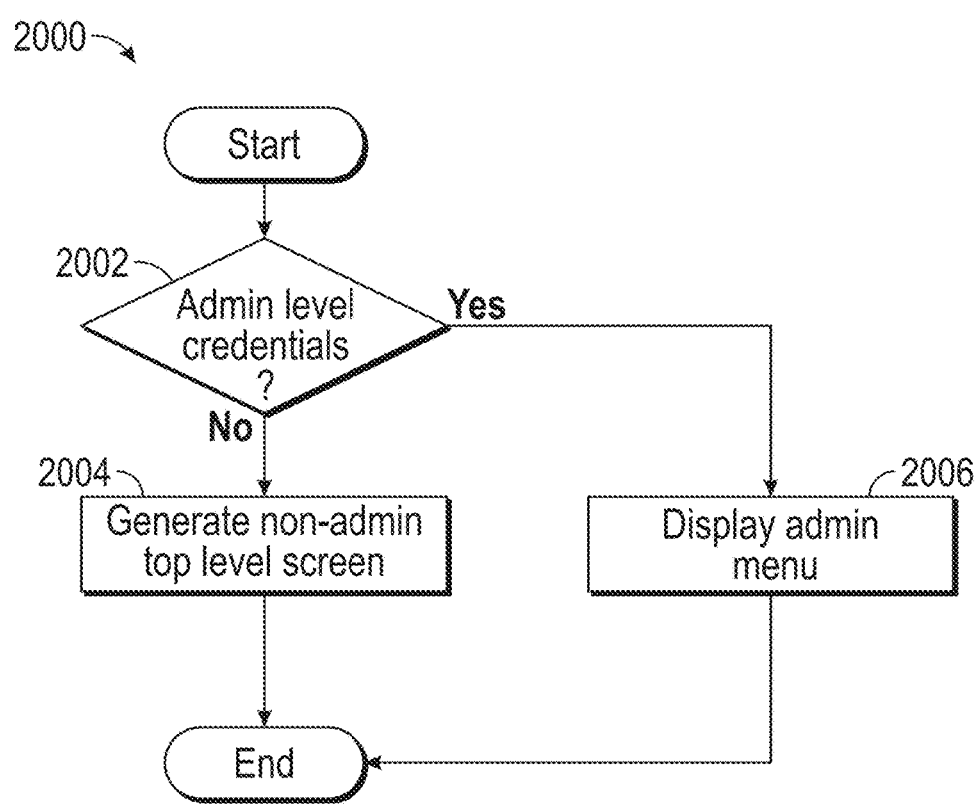
FIG. 20B is a flow diagram of exemplary methodology for securely providing an administrative panel display.

An exemplary top level display 500 is shown in FIG. 5. The top level display 500 includes a top level panel 501 where a first plurality of graphical interfaces for selecting modules (module selection graphical interfaces) such as a patient list graphical interface 502, a report generation graphical user interface 504, an images query graphical interface 506 and an administrative panel graphical interface 508 are displayed. The graphical interfaces among the first plurality included in the top level display will depend upon the modules associated with the user name. For example, as shown in FIG. 20A, the top level display can include an encounter query graphical interface if this module is associated with the user name.

Figure 7:
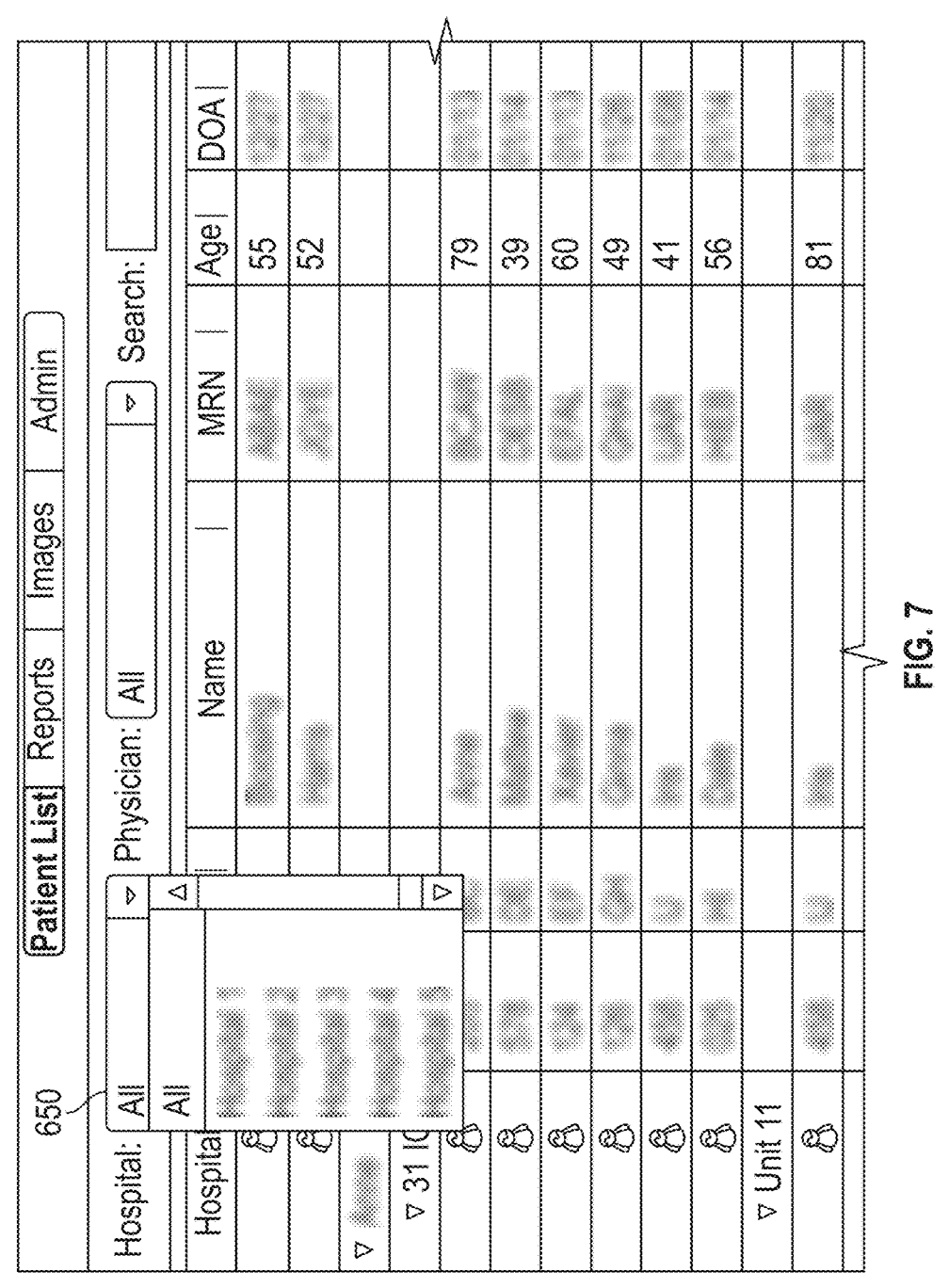
Figure 8:
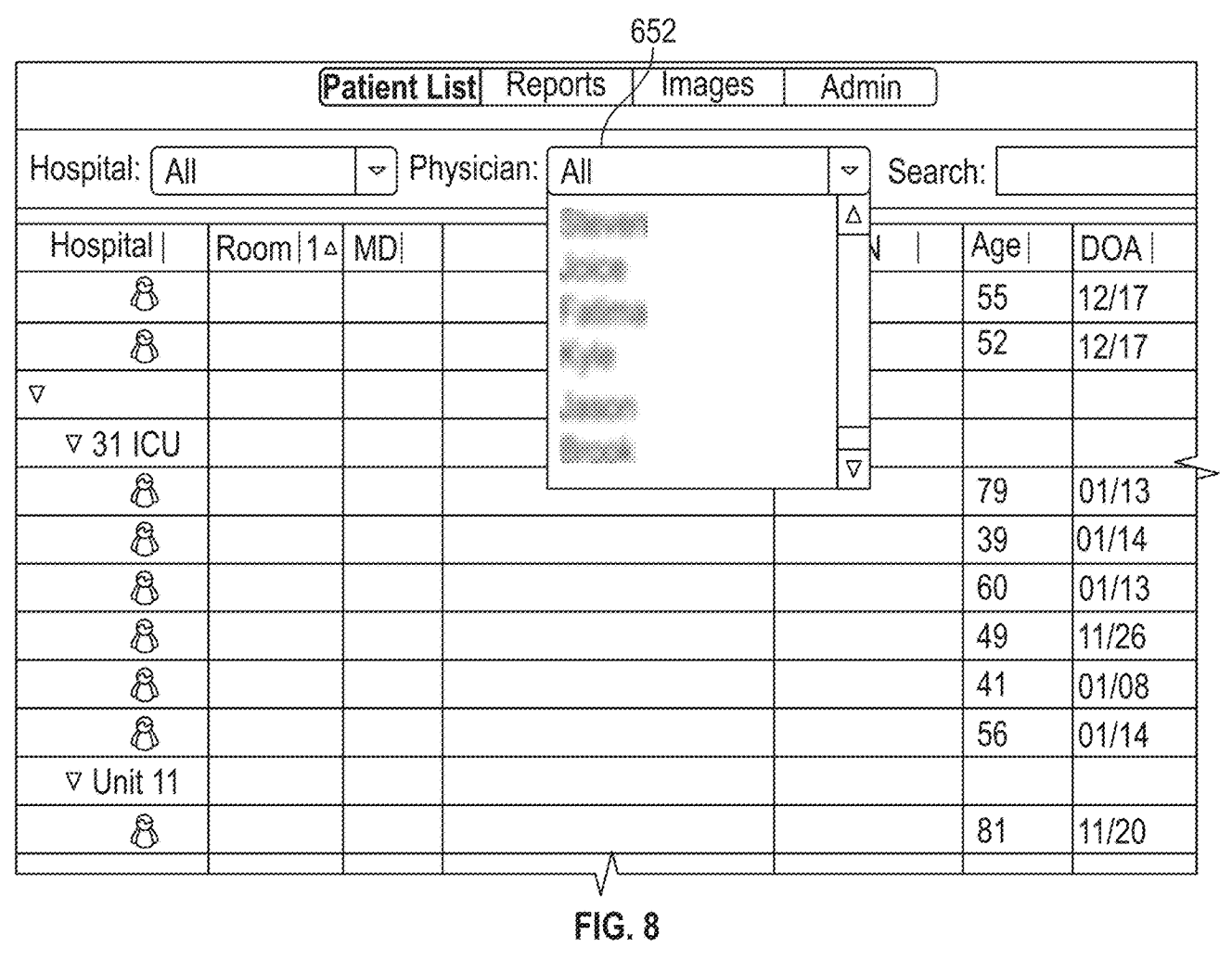

In the example top level display 500, the patient list graphical interface 502 has been selected, so the patient list display 503 is also generated below the top level panel 501. The patient list display 503 includes a plurality of graphical interfaces for generating displays associated with the patient list module which are subsequent in hierarchy to the top level display. As shown in FIGS. 5-6, the graphical interfaces include a print portable document format (PDF) graphical interface 510, an add patient graphical interface 512, an edit patient graphical interface 514, a remove patient graphical interface 516, an open text filter field 654 and a plurality of graphical interface filters 650, 652 including a plurality of selectable patient attributes. Based upon the information entered in the open text filter field 654 and the patient attributes selected by the filters, the patient list display 503 can be updated to include one or more identifications of patients (such as patient names) and patient attributes associated with the patient names. The patient attributes displayed in the patient list display include a hospital or care facility associated with the authentication credential (user name), and a type of unit or physician group associated with the hospital or care facility. As shown in FIGS. 7-8, the first and second filters can be pull down tabs including a list of selectable hospitals, units associated with each of the hospitals and physicians. The patient list display can be further filtered based on several criteria, including but not limited to provider, location of service, subspecialty group, among others. It should be noted that although the graphical interfaces are shown here as buttons or pull down tabs, one of ordinary skill in the art should appreciate that the interfaces can be other types such as radio buttons, check boxes, etc.

Figure 14:
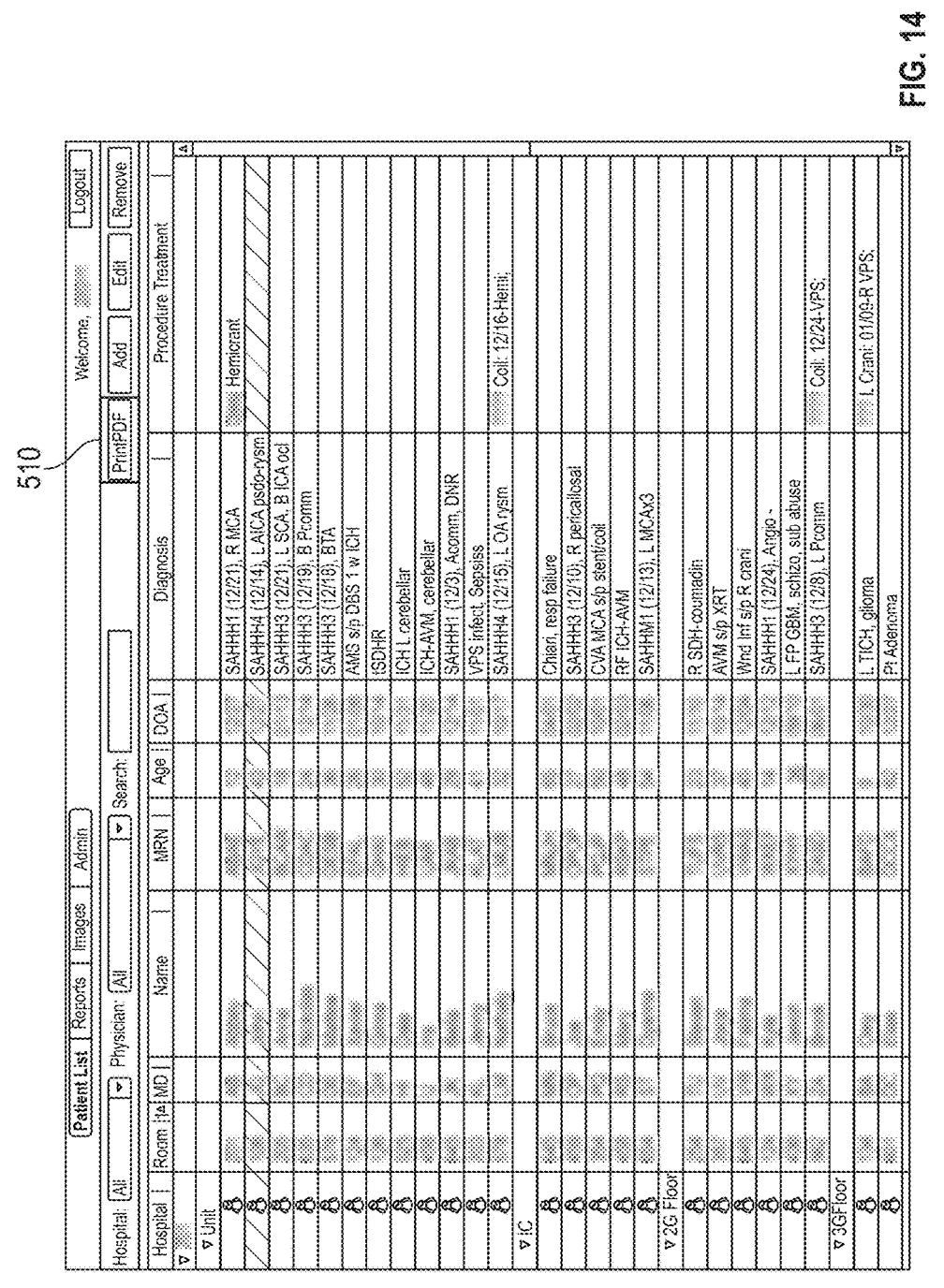
Figure 15:
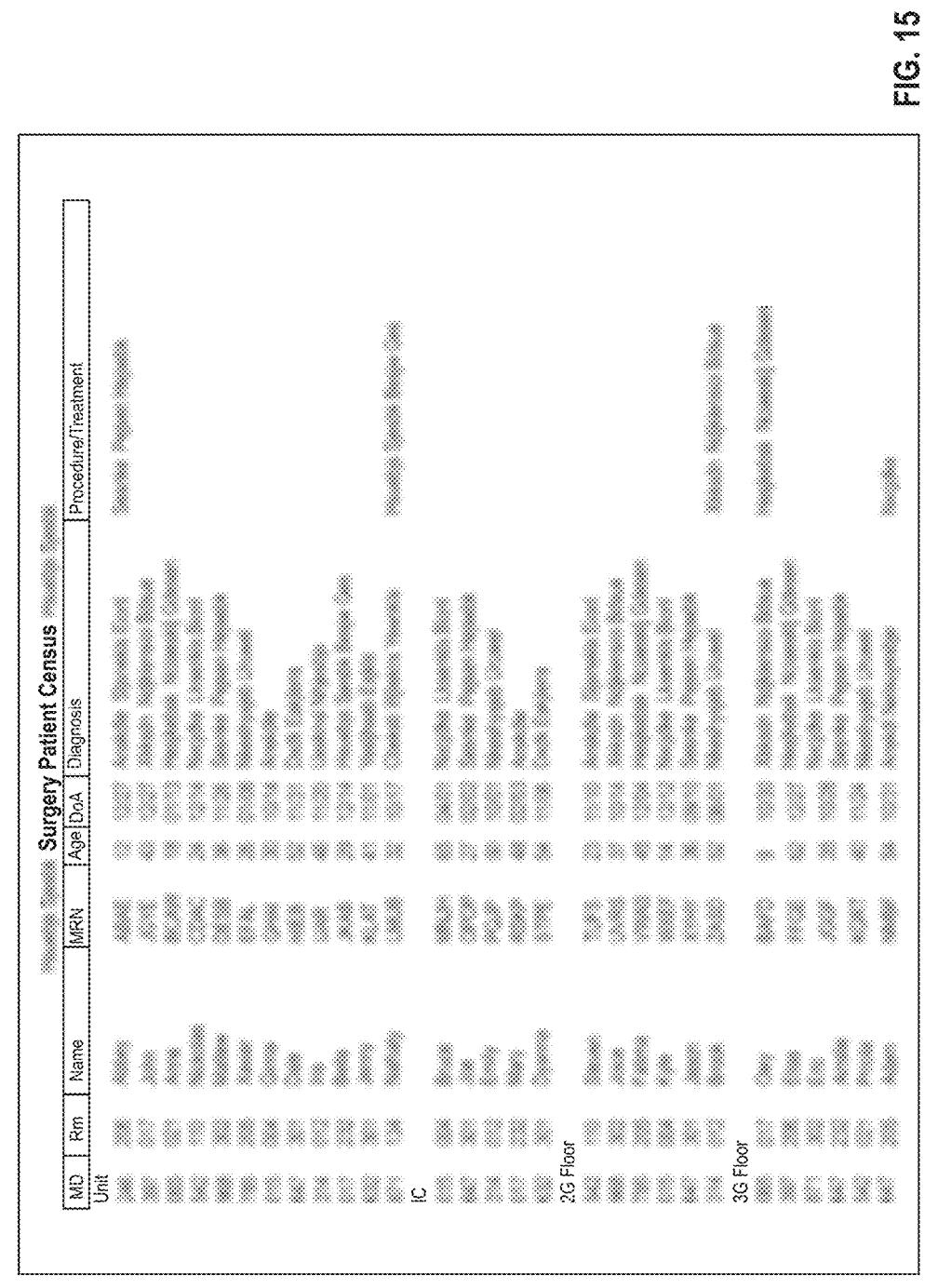

When the PDF graphical interface 510 is selected (FIG. 14), a PDF document including a filtered patient list based upon the patient attributes selected in the filters is generated as shown in FIG. 15.

Figure 10:
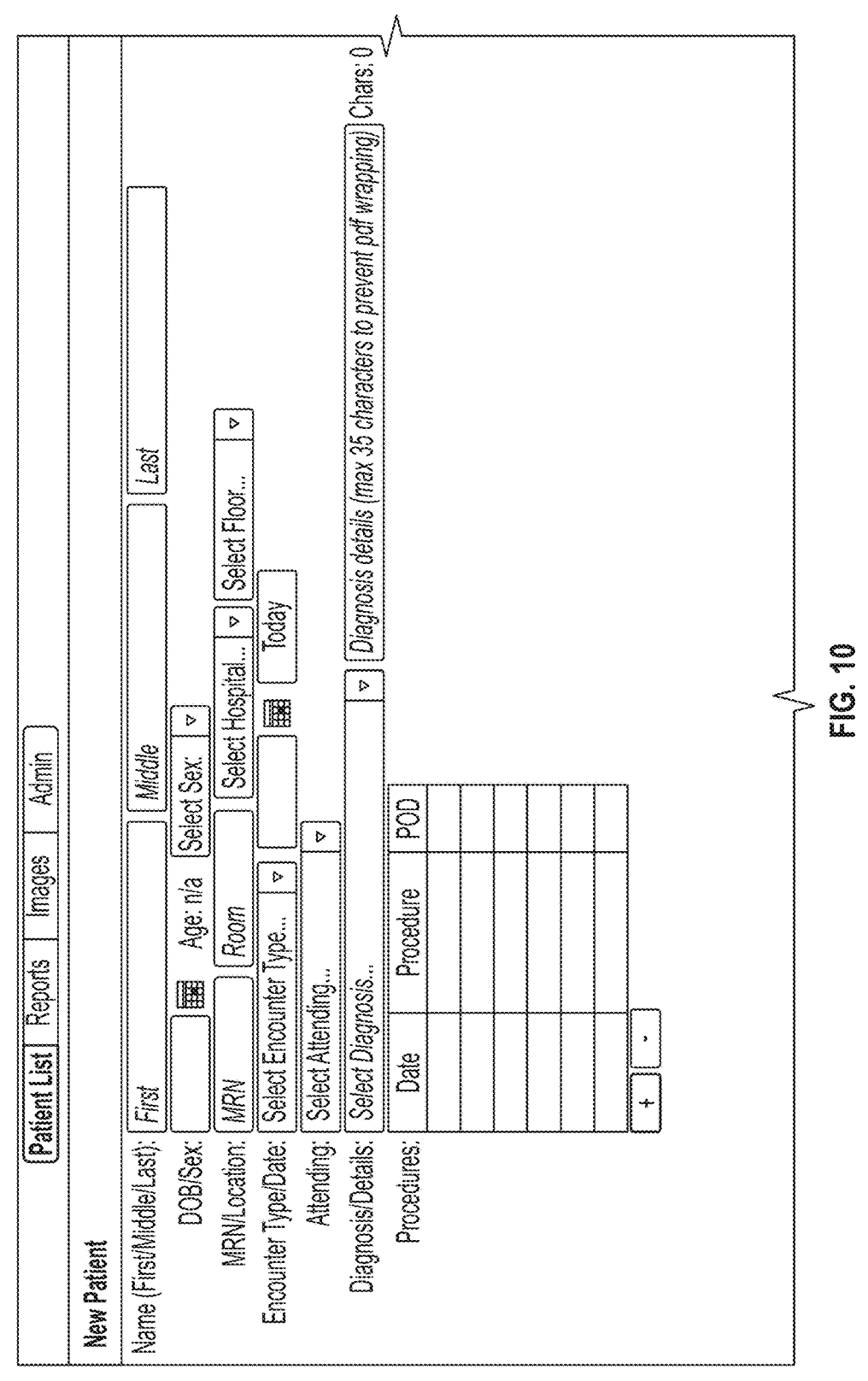
Figure 11:
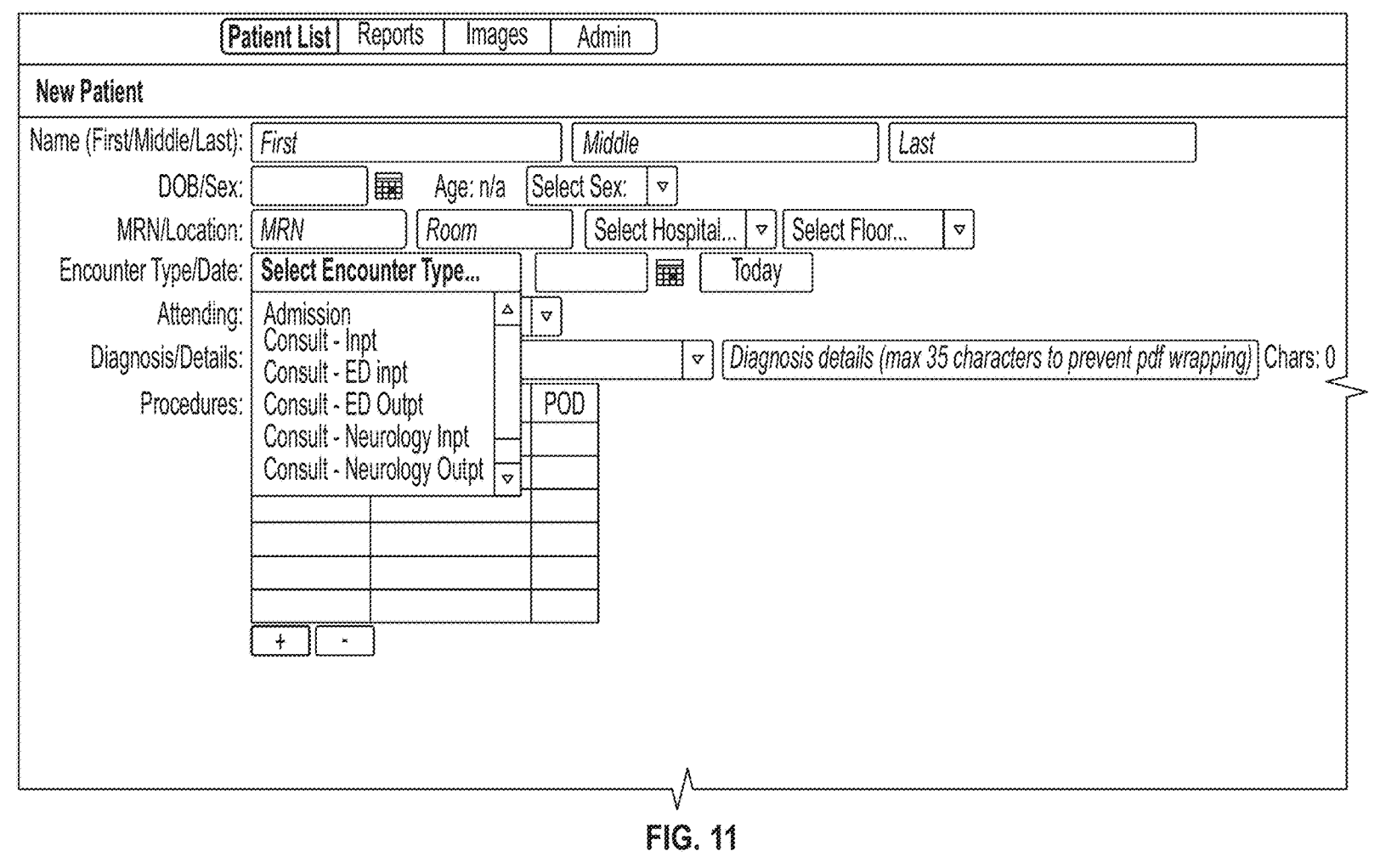

Referring to FIGS. 5 and 9B-13, when the add patient graphical interface 512 is selected, an add patient display shown in FIG. 10 is generated. The add patient display is subsequent in hierarchy to the patient list display. The add patient display includes a plurality of open text filter fields for receiving data, and a plurality of classifying graphical interfaces (pull down tabs) including a plurality of selectable options for classifying a new patient. The classifying graphical interfaces includes encounter type graphical interfaces including encounter types for a care episode for the patient (FIG. 11), diagnosis graphical interfaces including diagnoses for the care episode (FIG. 12), and a procedure graphical interface field for entering data relating to a new procedure or modifying data relating to an existing procedure (FIG. 13). The procedure graphical interface includes a graphical interface for entering a physician name, a role of the physician and selecting from a list of procedure types. An edit patient display similar to the add patient display can be generated when the edit patient graphical interface 514 is selected.

Figure 16:
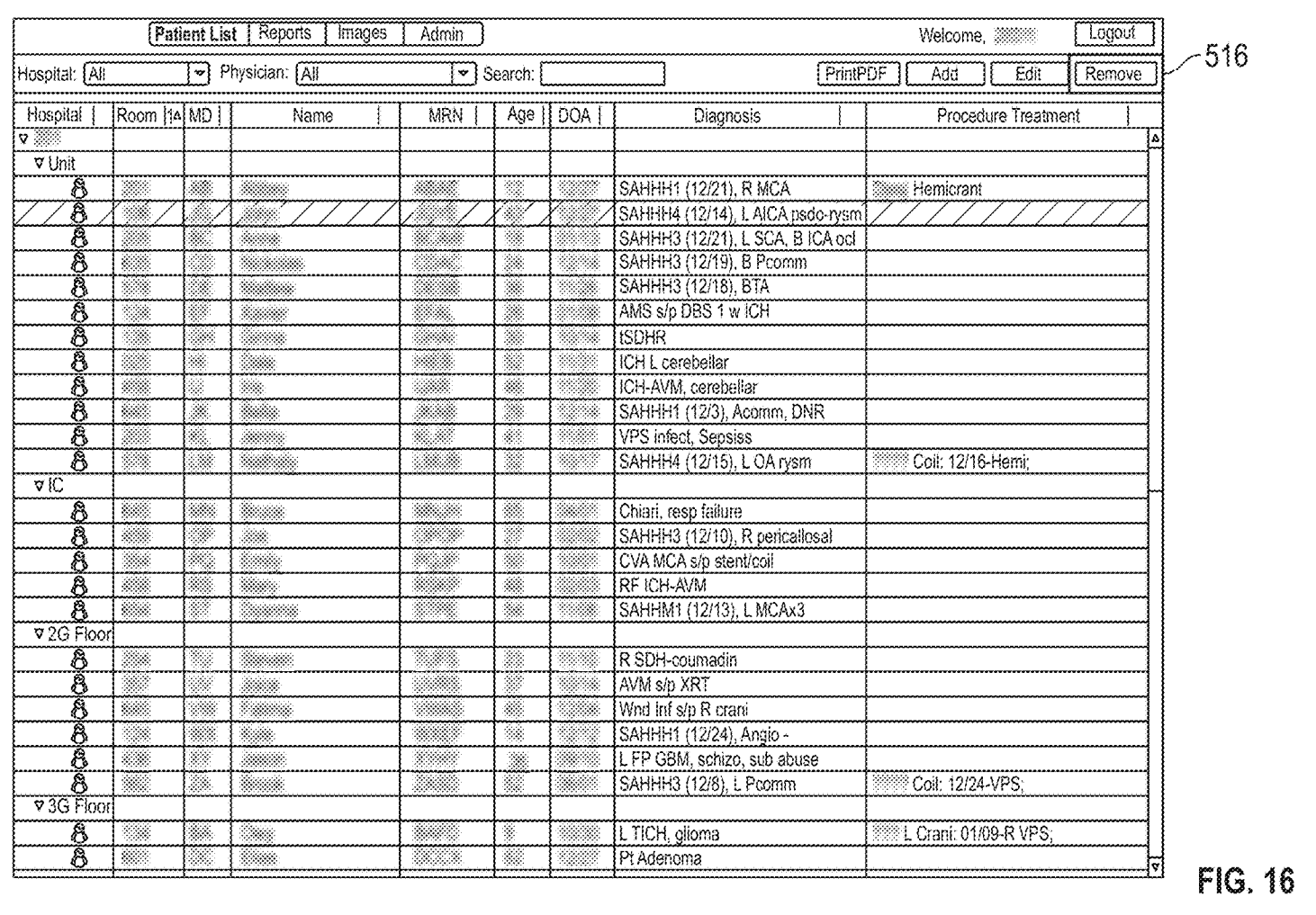
Figures 17, 18:
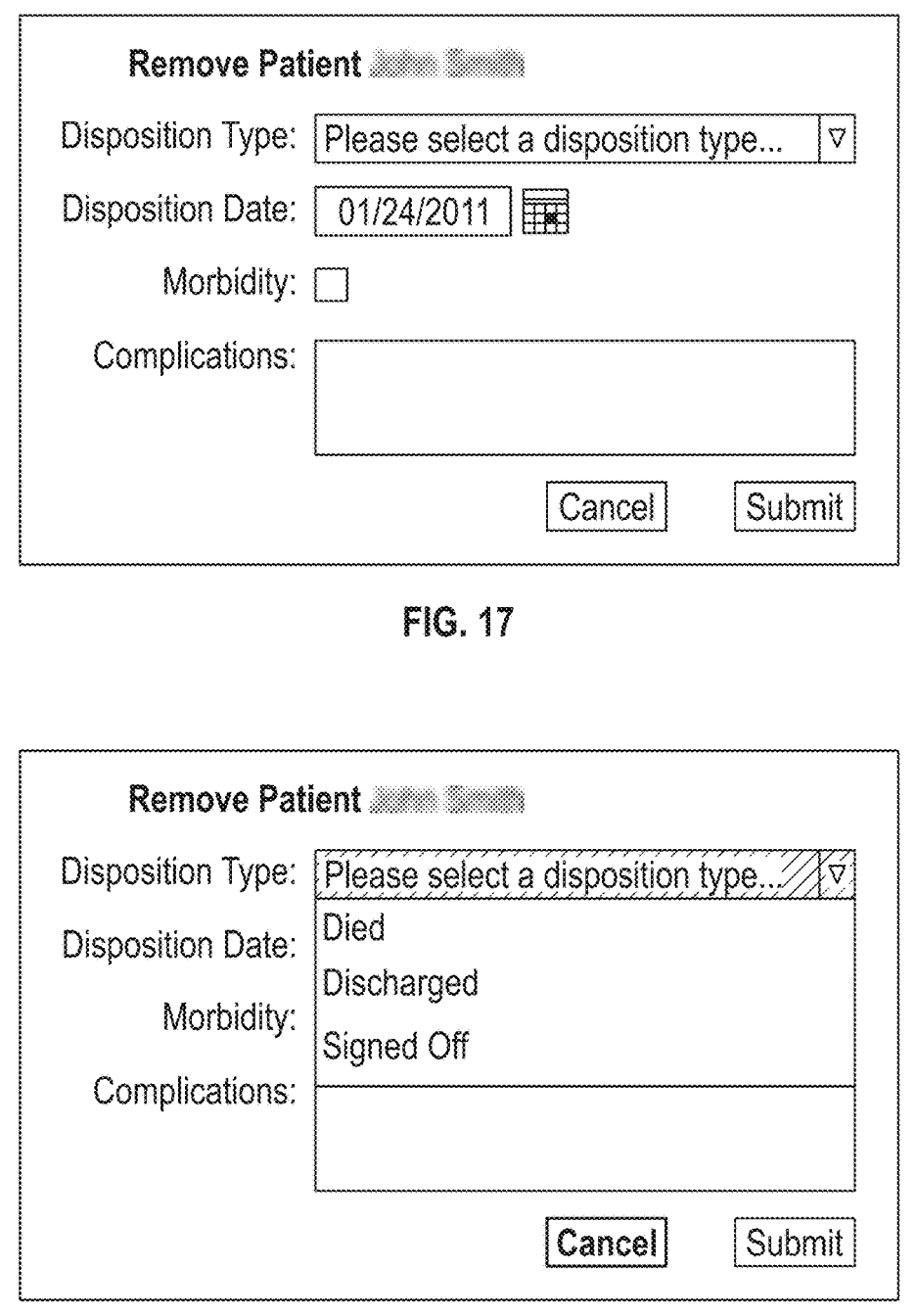

Referring to FIGS. 5 and 16-19, when the remove patient graphical interface 516 is selected, a remove patient display shown in FIG. 17 is generated. The remove patient display is subsequent in hierarchy to the patient list display. The remove patient display includes a disposition type graphical interface including a list of disposition types for a care episode for the patient (FIG. 18), a tag option (such as a check box) for indicating a particular episode of care as a morbidity, and an open text field for providing additional details (FIGS. 18-19).

Figure 9A:
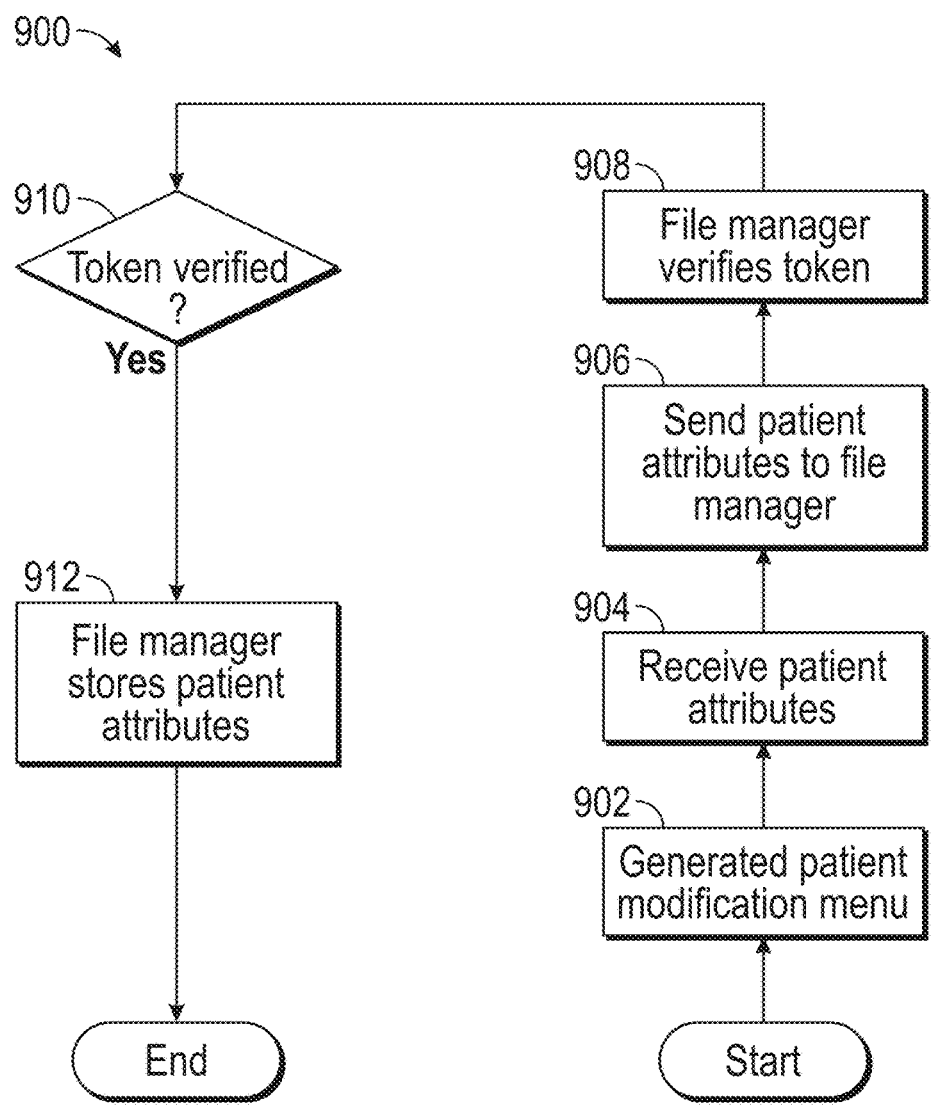
FIG. 9A is a flow diagram of exemplary methodology for modifying patients in the patient list display.
Figure 9B:
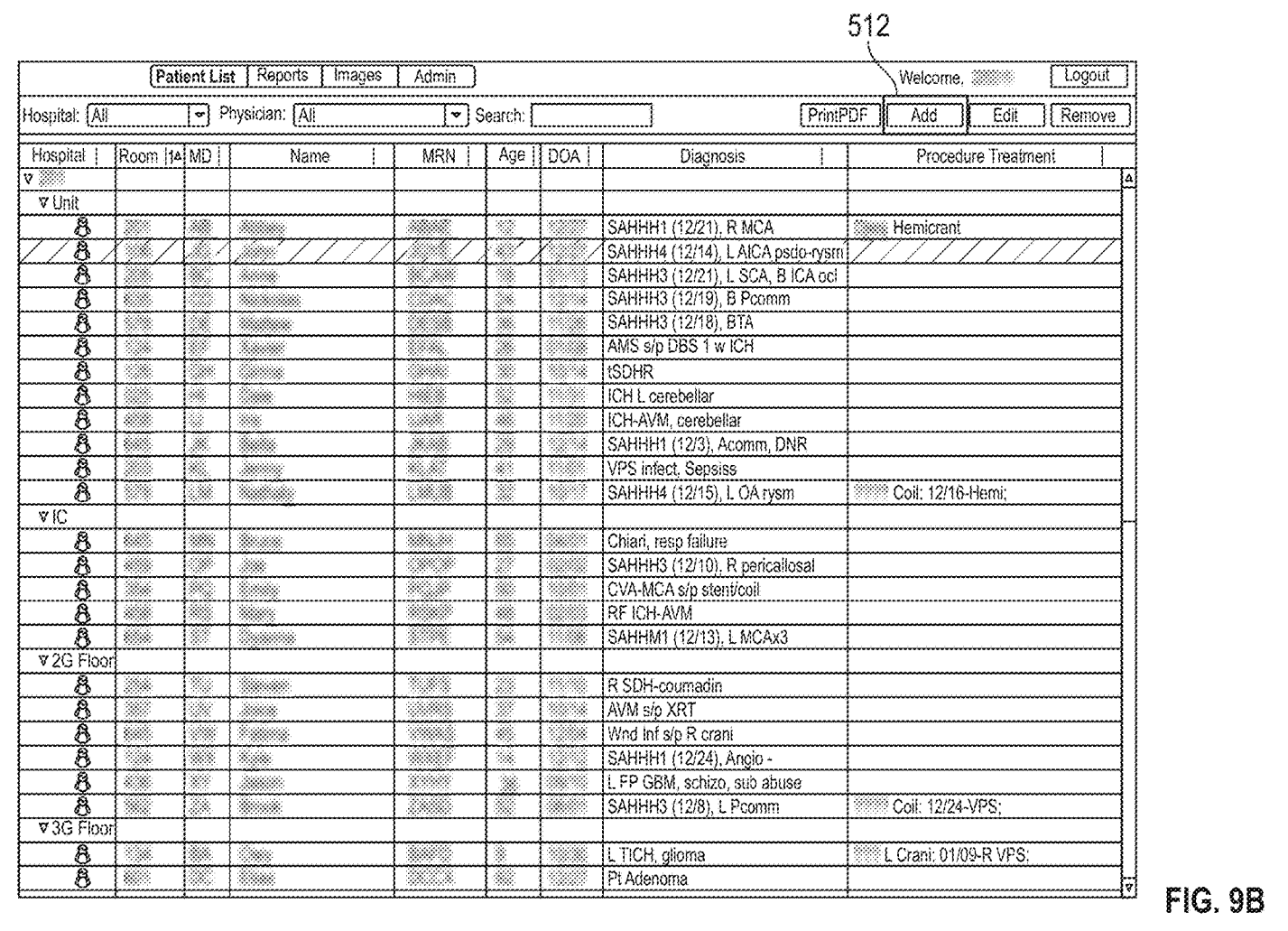

Referring to the flow diagram of FIG. 9A, an exemplary methodology executed by the patient list manager device and the client device for modifying patient data in the patient list database will be discussed. At 902, the client device generates a patient data modification menu such as the add patient display, edit patient display or remove patient display based upon selection of the user of the respective graphical interface. At 904, the user captures patient attributes via the modification menu. The captured patient attributes can include, but are not limited to, patient demographics, categorical diagnose(s), dates of service, treating physician(s), surgical procedures, operating surgeon(s) and assistant(s), and location of care episodes (facility, unit, and room number), among other information (FIG. 10). At 906, the patient attributes are encrypted and sent to the file manager device as a resource request including the token obtained at 416 or a different token.

At 908, the patient list manager device receives the resource request and verifies the token similarly to the process at 420. If the token is verified (YES at 910), the patient list manager device stores the patient attributes in the patient list database. The information in the resource request such as the user name is used when storing the patient attributes. Here, the patient list manager device can decrypt the patient attribute and re-encrypt it before storing it in the patient list database. The system can use a variety of techniques for securing data at rest including, but not limited to, disk encryption and transparent database encryption. If the token is not verified (NO at 910), the patient list manager device can redirect the client device to the login screen as in 406-408.

Returning to FIG. 3C, the portions of the patient list manager device which execute the methodology for modifying patient data will be discussed. The transceiver 352 of the patient list manager device 350 receives a patient data modification request from the patient list manager client device 372 via the network 105. The controller 354 is configured to modify the data in the patient list database that is associated with the user name in accordance with the patient data modification request. Particularly, the controller 354 can modify one or more of the patient attributes associated with one or more of the patient identifications indicated in the patient data modification request (edit patient display); add a new patient identification and patient attributes associated with the new patient identification to the patient list database (add patient display); and classify one of the patient identifications associated with the user name from the patient list database as removed by, for example, adding a tag to an episode of care to indicate a morbidity.

As discussed above with respect to FIG. 2, the client device for accessing the patient list manager device 104 can be any web enabled mobile device (i.e. cellular phone, tablet computer, etc.). However, mobile device specific applications can provide richer user experience (FIGS. 33-37) on specific device clients. Such applications make a large majority of the functionality available in the web-based offering accessible via a local secure mobile device application that communicates with the patient list manager server backend on the cloud. Viewing the patient list and filtering the list by user specified criteria and adding new patient care episodes at the point of care are among the functions that can be carried out via a device specific mobile application (FIGS. 33-37).

Returning to FIG. 5, when the administrative panel graphical interface 508 is selected, an administrative panel display subsequent in hierarchy to the top level display is generated. An exemplary administrative panel display is shown in FIG. 20A.

Preferably, the administrative panel graphic interface 508 will not be shown in the top level display or the administrative panel display not generated unless the user name is determined to have administrative level privileges. That is, the administrative panel should only be available to users with appropriate credentials enabling the management of users, and the data populating the facility, unit, diagnosis, procedure, and disposition tables, among other functionality (FIGS. 21-28). Referring to the flow diagram of FIG. 20B, an exemplary methodology for determining whether to include the administrative level functionality (admin panel graphical interface 508) in the top level display will be discussed. At 2002, the patient list manager device determines if the user name associated with the token has administrative level credentials. For example, the patient list manager can pull the user name in the memory or patient list database to determine its credentials. If the user name has administrative level credentials (YES at 2002), then at 2006 the top level display including the administrative panel graphic interface 508 is generated. If the user name does not have administrative level credentials (NO at 2002), then at 2004, a top level display not including the administrative panel graphic interface 508 is generated. For example, in a case in which the client device is accessing the patient list manager via a website, based upon the determination at 2002, the code sent back to the client device for rendering a top level display may or may not include the interface 508.

Returning to FIG. 3C, the portions of the patient list manager device which execute the methodology for determining whether to include the administrative level functionality (admin panel graphical interface) in the top level screen will be discussed will be discussed. The controller is further configured to determine if the user name in the resource request is an administrative level user name. When the user name is determined to be an administrative level user name, the controller: determines a plurality of user names that are associated with the administrative level user name and all data associated with each of the plurality of user names, encrypts the data and sends it to the remote patient list manager client device during the secure communication session.

The client device can generate an administrative level data modification request (FIGS. 21-28) and an audit log request that are received by the patient list manager device transceiver. The controller is configured to modify the data in the patient list database that is associated with the administrative level user name in accordance with the administrative level data modification request and to generate encrypted historical usage information associated with the administrative level user name to be sent to the remote patient list manager client device during the secure communication session over SSL or TLS in response to the audit log request. The patient list manager client device can decrypt the data.

Referring to FIGS. 20A and 21-28, the administrative panel display can include an audit log graphical interface and a list of a plurality of top level parameters which can be modified. When the audit log graphical interface is selected, historical usage information (an audit log) is displayed as shown in FIG. 20A. The audit log is implemented to track activities of all users.

When one of the top level parameters is selected, a respective modification display for the selected top level parameter is generated. The list of the plurality of top level parameters which can be modified includes: diagnoses included in the diagnosis graphical interface (modification display shown in FIG. 21), disposition types included in the disposition type graphical interface (modification display shown in FIG. 22), encounter types included in the encounter type graphical interface (modification display shown in FIG. 23), hospitals and physicians included in first and second graphical interface filters of the patient list display (modification displays shown in FIGS. 24-25), procedure types included in the procedure graphical interface of the add/edit patient display (modification display shown in FIG. 26), types of the unit associated with the hospital or care facility (modification display shown in FIG. 27), and users with privilege to access the patient list manager device (modification display shown in FIG. 28). The modifications displays for each of the top level parameters includes a graphical interface displaying respective data and a free text input field for filtering data displayed for the respective top level parameter.

Figure 29A:
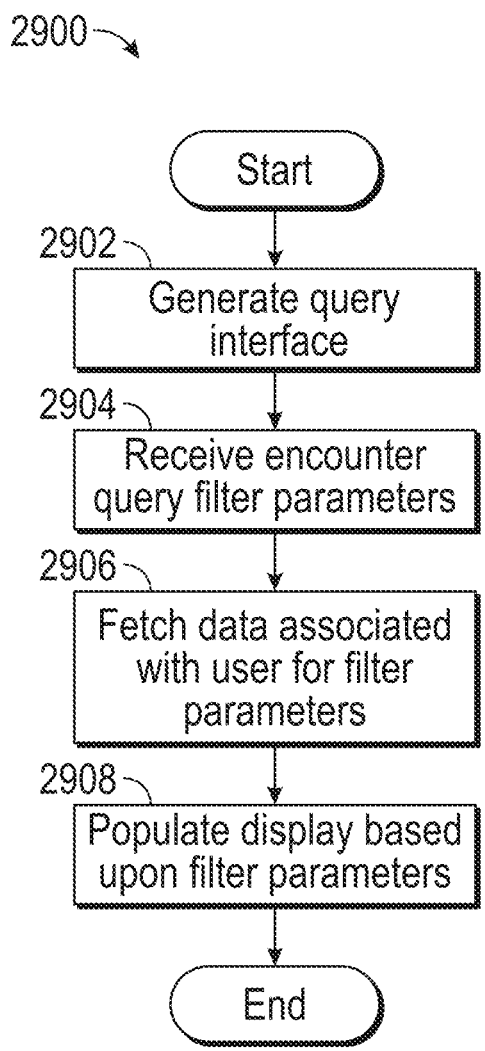
FIG. 29A is a flow diagram of exemplary methodology for securely providing an encounter query display.

Referring to the flow diagram of FIG. 29A and the display screen shot of FIG. 29B, a historical encounter query module for the patient list manager will be discussed. Clinical and business intelligence can be a critical aspect of quality and operations improvement in medicine or for that matter any business. Without the ability to access data about historical activities, physicians, providers and business managers are left to operate their practices on subjective anecdotal evidence rather than objective measures and data. The historical encounter query module provides subscribers with appropriate credentials with access to a query engine that allows them to obtain information about prior care episodes for authorized purposes only. The query interface, which can be customized, allows users to search for current and historical patient encounters meeting various criteria. The query module leverages the structured data captured in each patient care episode within the database for the patient list manager. Queries can be done with any number or combination of criteria and/or operators including but not limited to and, or, etc. Free text queries for one or more fields can also be carried out alone or in combination with structured element query fields. Criteria settings from any given query can be saved providing the ability to leverage time invested previously in entering desired query criteria for queries that may need to be run routinely. Results can be viewed in a list format (multiple patients) or individually in a patient detail view.

The historical encounter query module can be implemented within the patient list manager device or it can be a separate device/application similar to the diagnostic image manager and RCM devices. In a case in which the query module is implemented within the patient list manager, the top level display can include an encounter query graphical interface 2950 for selecting the encounter query module. When the encounter query graphical interface 2950 is selected, a query engine interface display including query parameters for querying historical clinical encounters is generated at the client device (see step 2902). The query filter parameters include date ranges associated with procedures and admissions, encounter types, facility names, text fields for entering medical service providers, disposition types and morbidity. Query filter parameters entered by the user are received by the file manager device (see step 2904). At 2906, the patient list manager device fetches data associated with the user and the query filter parameters from the patient list database, encrypts the data and sends it to the client device. At 2908, the client device decrypts the data, and a results area in the query engine interface display is populated with the decrypted data.

In a case in which the historical encounter query module is implemented within the patient list manager device, the transceiver of the patient list manager device receives an encounter query request from the patient list manager client device, the encounter query request includes one or more parameters for clinical encounters. The controller generates historical clinical encounters associated with the administrative level user name and based upon the one or more parameters to be sent to the remote patient list manager client device during the secure communication session. The data itself may be encrypted before sending and the client device will subsequently decrypt it and display the data to the user. The one or more parameters for clinical encounters include date ranges associated with procedures and admissions, encounter types, facility names, one or more physicians, disposition types and morbidity.

Referring to FIG. 30, a report generation module for the patient list manager system will be discussed. The report generation module can leverage the patient list manager to generate at least three types of reports: a morbidity and mortality (M&M) report; a residency operative experience report; and a program case log. The report generation module can be implemented within the patient list manager device or it can be a separate device/application similar to the diagnostic image manager and RCM devices. In a case in which the report generation module is implemented within the patient list manager, the top level display can include a report generation graphical interface 3000 for selecting the report generation module. When the report generation graphical user interface of the top level display is selected, a report generation display including a plurality of report graphical interfaces, a report filter graphical interface for filtering a report to be generated and a graphical interface for generating the report as a PDF document is generated. The report graphical interfaces are for selecting a type of a report to be generated and include a M&M report selection graphical interface, a resident operative experience report selection graphical interface, and a program case log report. Each of these three reports will be discussed below.

The M&M Report

The M&M report can meet the need attending physicians, physicians in training, and other providers often have to track information about patients they care for and any complications or deaths that might occur. The M&M report can be used to report captured information about and flagged care episodes where there has been some morbidity or mortality. For example, the information may have been captured by being entered via the remove patient display at the point of care when a patient is transitioning care settings (FIG. 19). The information could also be captured at any other time during the continuum of care. Reports searching for patients flagged as morbidities or mortalities can then be run and used for quality improvement, outcomes assessment, and resident physician teaching in graduate medical education programs.

The Residency Operative Experience Report

Residency programs are required to capture clinical and surgical encounter and case volumes across multiple facilities for accreditation purposes. This data is frequently captured via manual data abstraction and capturing it can be quite time consuming and difficult to coordinate. The data collected manually can be highly variable in quality and is often inaccurate and incomplete. The data collection and the usefulness of the data are also frequently plagued by a significant time lag due to the tedious nature of duplicative manual data capture and entry. Some residency programs employ individuals with this manual data capture and entry as one of their job duties. Other residency programs require residents themselves to capture this data, often times manually, followed by rekeying of the data into third party systems. In the later scenario, the coordination piece of the data collection process is difficult and time consuming and often is carried out by an administrator in the residency program that polices the entry of clinical and surgical encounter data entry by the resident physicians. These issues and challenges are further exacerbated by the fact that resident physicians in many residency training programs go to multiple training sites or facilities that can be otherwise un-affiliated and on different medical records management systems which might be paper based or electronic.

The report generation module leverages the structured data captured at the point of care via the patient list manager to automate the residency program data capture and reporting for accreditation purposes eliminating several steps of painful data collection, data set merging, and data set analysis that is otherwise required. Further, the need to police the entry of case and encounter data into third party systems is also eliminated. Encounter and surgical case volume reports, even across disparate facilities, for residency program accreditation and re-accreditation purposes can be generated in the format required by the Accreditation Council for Graduate Medical Education, the residency program accreditation entity in the United States, in a turnkey fashion. Canned reports can be populated into a PDF, which can be printed (if a hard copy is desired) or viewed in a graphical user interface. Individuals with appropriate credentials and user privileges can also download data for submission to the governing accreditation entities in electronic format. Within the system, the data can also be manipulated and output in other ways useful to the residency program for resident education (i.e. for evaluations to assess the experience a resident has had to date, to assess the clinical experience at various training sites, to guide faculty hiring needs, among many others).

Case Log Reports

For years surgeons have kept manual surgical case logs which effectively served as paper based "databases" of the surgeries they have completed historically. All surgeons and anyone who has rotated on a surgical service is all too familiar with these composition books and ledgers with patient stickers and hand written notes about each surgery done and which physicians or other providers participated in the case. These physician or provider centric surgical case logs are not typically maintained as a part of the official legal facility or hospital based medical records (i.e. in the medical records system), but instead are, in many cases, manually maintained by the physician or other provider. The surgical case logs serve as a historical record or database of the surgical cases each individual physician or other provider participated in previously (as far back as they have maintained records) up to the current time. The historical information is often needed for future reference, board certification, hospital credentialing, and to document the training of resident physicians as well as the experience provided by a particular residency training program.

Leveraging data captured at the point of care with the cross-facility patient list manager, surgeon case logs reports can be generated in a turnkey fashion. Case logs can also be generated for other providers that might participate in surgeries (i.e. physician assistants, nurse practitioners, etc.) as well as residents and medical students who frequently assist in surgeries that occur in academic medical centers. In fact, graduate medical education in the United States, particularly in surgical specialties, has become increasingly focused on having residency programs quantify the patient care experience of physicians during residency training with surgical case logs as this provides documentation of the breath and depth of each resident physician's operative experience.

Moreover, at the time surgeons complete residency training, in many specialties, each new attending surgeon then enters into a period called the surgical case "board collection period." During this time period, these "board eligible" surgeons are required to i) gather information about the surgeries they ultimately complete during the first few years of their early careers and ii) submit this information to their specialty board as a part of the process of obtaining board certification in their surgical specialty. This creates a significant administrative burden as it typically requires manual data capture, it often involves re-keying duplicative data, and it frequently is accomplished by maintaining a paper based database for capturing this information. This tedious manual process is required simply because the data captured in the course of care provision resides in hospital and office paper records or information systems, neither of which are readily queryable directly by the surgeons for the purposes of complying with this required step in the board certification process.

Case log data is also something surgeons require when applying for privileges at any healthcare facility as a part of the credentialing process. Facilities have surgeons undergo this process in order to assess their competence and to determine whether they should grant a given physician privileges to i) admit patients; and ii) carry out invasive procedures within the facility. If a surgeon has not maintained the right information formatted correctly in his or her practice records historically, gathering this data can be painstaking and involve multiple phone calls and discussions with various gate keepers; the time required to reach the right personnel and the time it takes to get a report generated can be significant. In fact, in some cases, getting the necessary data can be impossible, particularly when access to healthcare information systems at a previous employer has ended. This issue is further exacerbated when a physician or other provider has been rendering their professional services at multiple unaffiliated facilities, as the process has to then be duplicated across facilities requiring interaction with a different set of gatekeepers at each facility.

In the surgical case log manager module, canned reports are made available to users. A few examples of the reports that a user might generate include reports that sort or group procedures by various criteria, including, but not limited to, type, billing code, category, etc. Data can be reported in a de-identified fashion or with patient identifiers. Various criteria can be specified to drive report generation including, but not limited to, patient demographics, location of surgery, dates of surgery, provider, type of surgery, specific procedures, specific procedure codes, co-surgeons, assistants, etc. Volume reporting by case type, billing code, and category is also available. Canned reports populate a PDF, which can be printed (if a hard copy is desired) or viewed in the graphical user interface. Access to various reporting functionality is managed on a need to have basis; only users with a business or clinical need for certain reporting functions are given such access and the local administrator for the subscription manages this.

Sign-Out Report

Sign-out is a critical interaction for the transfer of key patient information between care teams at shift changes for physicians and other providers. In the wake of the Institute of Medicine's 2000 Report, To Err Is Human, and the resultant resident duty hours restrictions and focus on fatigue related medical errors, medical and surgical practice in many care settings has moved towards more of a "shift-work" paradigm. As such, more and more attention is now being focused on ensuring safe transitions in patient care and the most effective means of communicating important details about each patient between providers at shift change. Providers are increasingly finding themselves in the role of caring for patients for whom they are not the primary provider ("cross-covering" for their colleague's and their partner's patients); thus, they potentially lack intimate familiarity with each patient's situation, magnifying the importance of effective communication during handoffs in patient care.

Sign-out is yet another opportunity to introduce misinformation or to fail to effectively communicate vital information; thus, the more standardized these transitions in patient care teams can be made, the more likely patient care teams are to avoid inadvertent lapses in communication that can lead to medical errors. The sign-out report generated by the report generation module can be a tool that integrates into the patient list manager and helps physicians and other providers better execute and standardize their sign-out communications. There are a few key items that must be communicated during sign-out; a partial listing of these includes (but is not limited to): Patient condition and code status; Current diagnoses and recent procedures; Current significant medical and surgical issues; Items requiring provider action during the next shift; Patient care interventions that need to be ordered or completed: Tests and diagnostic results that need follow-up; and High-level plan of care and related action items. The sign-out report generated by the report generation module can provide a structured way for physicians and other providers to capture and share data facilitating smooth and effective transitions in patient care during care team handoffs. A sign-out report patient list with pertinent information previously abstracted and captured in the patient list manager system by a physician or other provider (i.e. data previously entered at the point of care) is viewed via a web browser (FIG. 5), via another client (i.e. a mobile device), or alternatively via a patient list sign-out report 'hard copy' printed out from the system (FIG. 15). The data populating the fields on the sign-out report patient list is used to help guide the physicians or other providers as they review the pertinent details about each patient during care team transitions (i.e. shift change). The patient list sign-out report aids the physicians or other providers with conducting their sign-outs and communicating the plan of care in a structured, standardized, and methodical fashion driven by the aid of a visual report populated with near real time cross-facility data.

Clinical Encounter Case Log

The Clinical encounter case log is similar to the surgical case log only it is focused on clinical episodes of care that are non-procedural (i.e. not patient surgeries) in nature. Individual physicians or other providers have a need for logs that capture their patient volumes, potentially across facilities, which can report care episodes individually or grouped by certain criteria for certain date ranges. This information is often needed for physician or other provider credentialing.

Figures 38, 39:
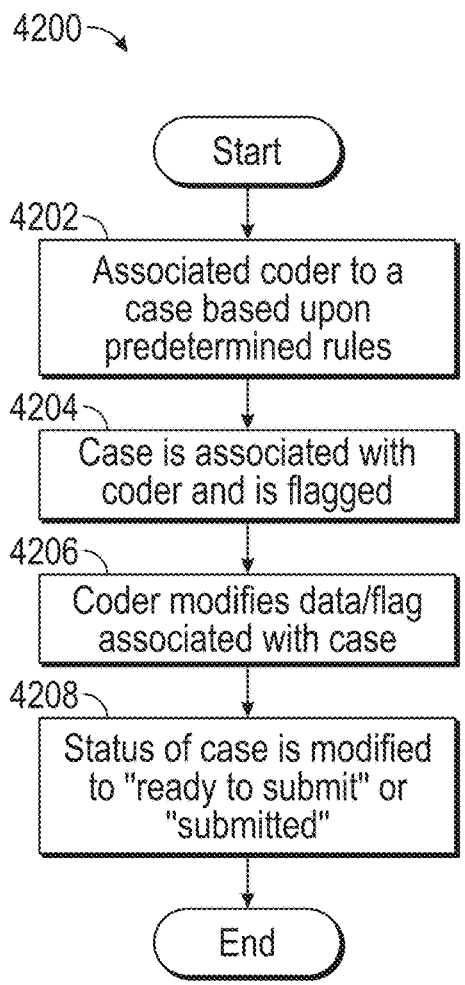
FIG. 38 is a screen shot of an example encounter volume statistics reporting dashboard example.
FIG. 39 is a flow diagram of exemplary methodology for operating a Revenue Cycle and Coding Operations Manager.

In the clinical encounter case log, canned reports are made available to users. A few examples of the reports that a user might generate include reports that sort or group care episodes by various criteria, including, but not limited to, type (i.e. admission, inpatient consult, emergency room consult, etc.), billing code, diagnosis, etc. Data can be reported in a de-identified fashion or with patient identifiers. Various criteria can be specified to drive report generation including, but not limited to, patient demographics, location of care episode, dates of care episode, provider, diagnosis, care team members, etc. Canned reports populate a PDF, which can be printed (if a hard copy is desired) or viewed in the graphical user interface in the PDF format or as part of a dashboard (FIG. 38). Access to various reporting functionality is managed on a need to have basis; only users with a business or clinical need for certain reporting functions are given such access and the local administrator for the subscription manages this.

Figure 31:
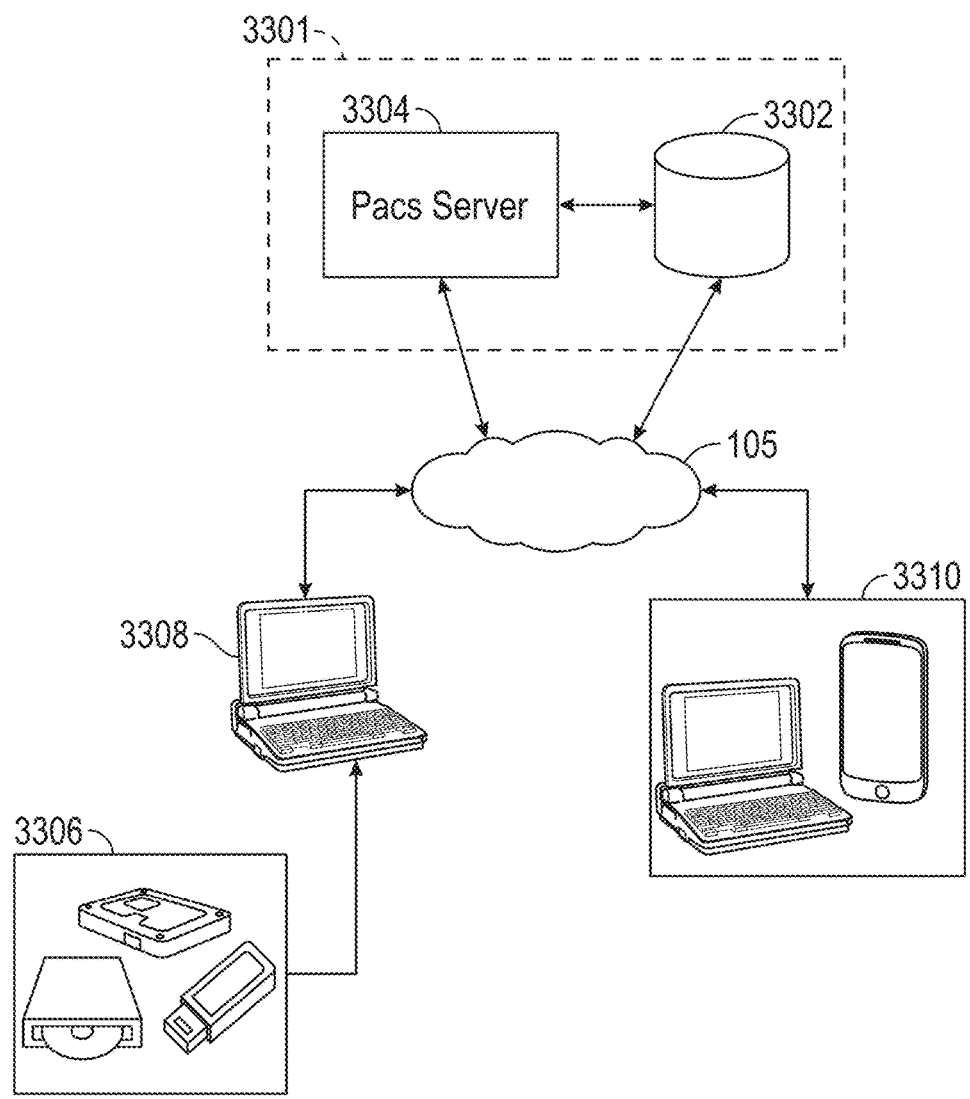
FIG. 31 is an illustration of a system for providing a patient list manager and diagnostic imaging management module according to exemplary embodiments.

Referring to FIG. 31, an exemplary embodiment of a patient list manager diagnostic imaging management module (imaging module) that can leverage the database in the patient list manager will be discussed.

Logistics for managing diagnostic imaging media can be challenging for medical service providers such surgeons who need to access imaging and view it firsthand rather than relying on the written or verbal interpretation of a radiologist. In addition, the availability of the diagnostic imaging at multiple points of care (i.e. in the office, in the operating room, in the emergency room, etc.) is highly desirable from a quality of care and cost of care perspective, yet fraught with logistical challenges and additional expense (delivery of the physical media to the point of care in coordination with appointment times, dates of surgery, etc.).

The information technology solutions for managing diagnostic imaging have evolved around radiologists and their workflow (i.e. the need to know an imaging study was completed such that they can interpret the films and generate a formal dictation on the images to be routed to the referring physician). Despite these advances, patients are often cared for by physicians and other providers that are unaffiliated with the imaging center where the diagnostic imaging was obtained or interpreted by a radiologist. In fact, in many cases, the physician or provider that orders a diagnostic imaging study may themselves be unaffiliated with the imaging center and work in a location physically different from (and under separate ownership than) the imaging center; moreover, this individual might, in the event it is indicated, then send the patient that underwent the diagnostic imaging study to be seen by a specialist in yet another separate physical location. Networks for the transport of diagnostic imaging are emerging, but are still in their infancy. In the large majority of cases, imaging is carried between physicians and other providers physically on actual physical media (i.e. on compact disc read-only memory). This can result in several inefficiencies (i.e. patient forgets imaging on day of appointment or surgery, provider forgets or loses imaging, etc.) and unnecessary expense (i.e. imaging is repeated because it is not available).

In instances when diagnostic imaging studies are successfully delivered on physical media to a point of care, there are also challenges with viewing the images. The file formats are often a specialized type that require specific viewing software not widely available on most computers. For this reason, the images on the physical media are typically packaged with an imaging viewer software. However, there is a highly fragmented market of software vendors that provide these viewers and with significant frequency the physicians or other providers are unfamiliar with the nuances of operating the specific vendor's software and, as a result, viewing the films becomes a time sink, injecting further inefficiencies into an already complicated process. This can be disruptive patient flow bottleneck in a busy clinic. Moreover, some of the imaging viewer software requires local installation and administrative rights to the operating system on the local computer, which is not something the physicians or other providers have in some care settings.

The imaging module employed can solve many of the above problems. In a system in which the imaging module is deployed, client devices 3308, 3310 communicate, via, a network 105 such as the Internet, one or more picture archiving communications and systems (PACS) servers 3304 and the patient list database 3302 associated with the file manager device.

Figure 32:
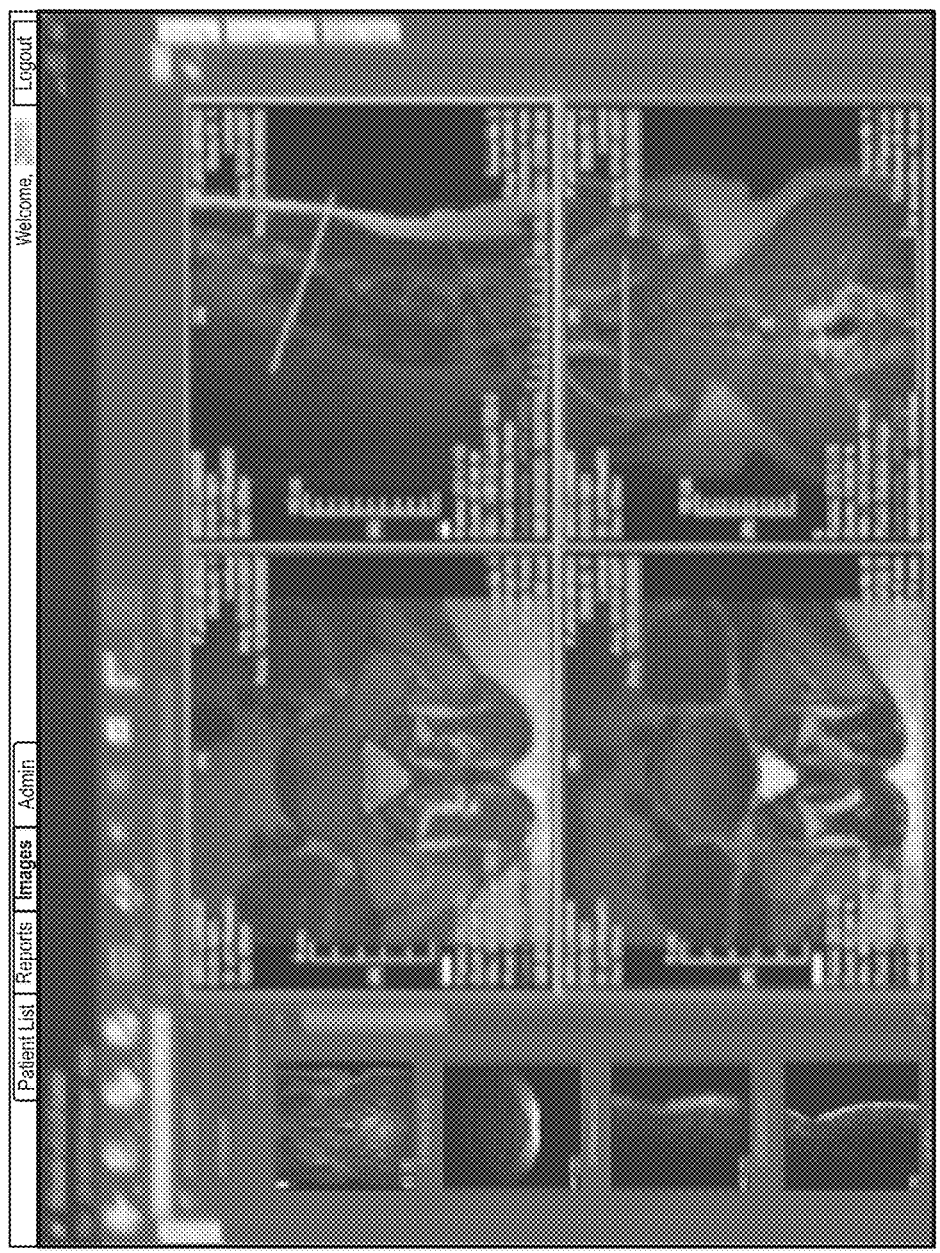
FIG. 32 is a screen shot of diagnostic imaging viewer interface.

A user at the client device 3308 has appropriate credentials for accessing the imaging module. Accessing the imaging module can be accessing a website hosted by a server or executing a client specific application stored at the client device. The client device 3308 includes images files 3306 formatted with the DICOM (Digital Imaging and Communications in Medicine) standard from physical media at any point of care. The client device 3308 can securely upload the encrypted imaging files to a memory space (cloud) provided by the PACS servers 3304 wherein the uploaded encrypted images and imaging header information are stored. The imaging module can index the uploaded images and tag them to the corresponding patients in the patient list database 3302. Another client device 3310 (having the appropriate credentials) can utilize an imaging viewer of the imaging module to render the images in the graphical user interface as shown in FIG. 32. This allows providers using the system to access, view, and manipulate images that are uploaded (traverse sections, zoom, window, etc.) at any point of care (or other location where they have a device that has Internet connectivity) at anytime as long as they have the appropriate credentials, thereby eliminating the need of interacting with a potentially unfamiliar diagnostic imaging viewer that accompanies the files on the physical media on which they come. Similar to the administrative panel display, the imaging module will preferably only be available to users with appropriate credentials.

When the imaging module is included in the patient list manager, the top level display can include a query graphical interface for activating the imaging module when selected. The imaging module includes an upload screen for uploading a diagnostic image associated with a patient to the patient list manager and an embedded DICOM viewer for viewing diagnostic images associated with the patient.

Figure 3C:
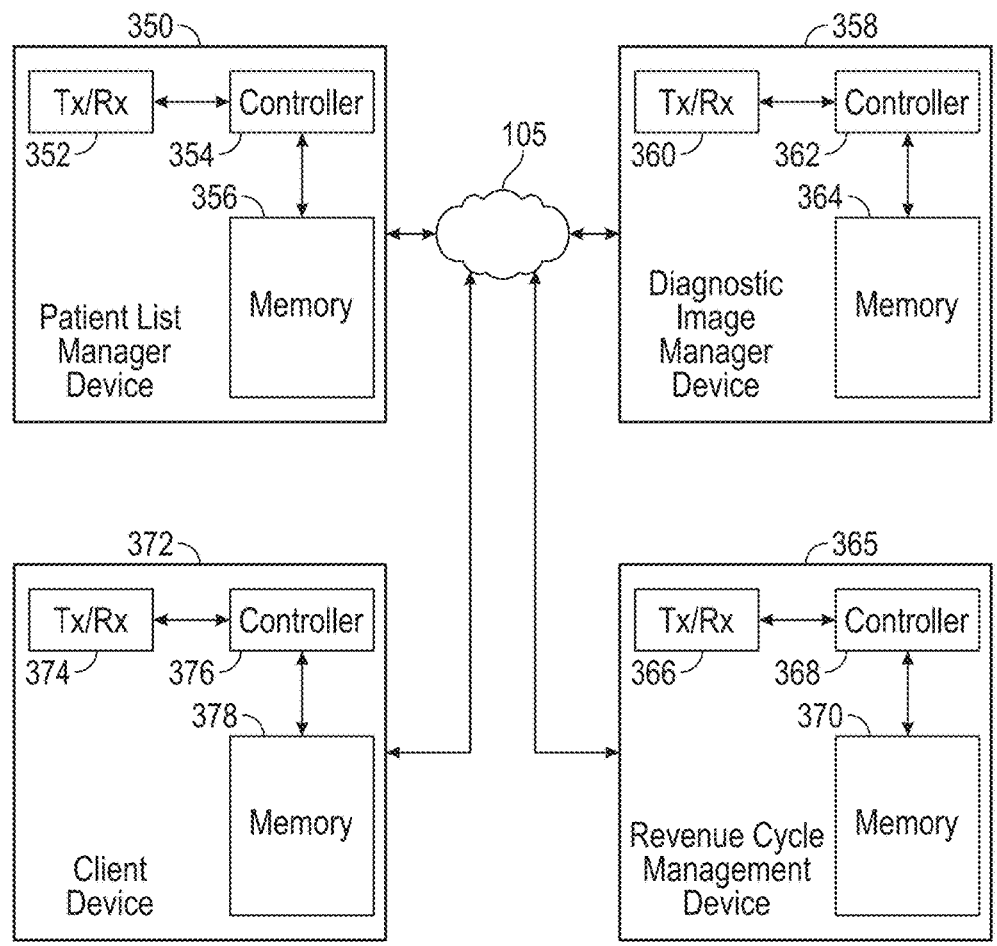

The imaging module can be employed as a module or submodule that interfaces with the patient list manager device as shown in FIGS. 3A-3B, or a separate diagnostic image manager device 358 as shown in FIG. 3C.

In one case, the server side of the image module is implemented by a diagnostic image manager device 358 separate from the patient list manager device 358 as shown in FIG. 3C. The diagnostic image manager device 358 can includes a transceiver 360, a controller 362 and a memory 364. The transceiver receives imaging resource request to access the PACS server from the client device. The imaging resource request can be an http request including a verification credential issued from a certificate authority such as a token and a user name. The imaging request can include a request to store a diagnostic image or a request to retrieve a diagnostic image. The imaging request preferably includes the diagnostic image as encrypted data when the imaging request is to store the diagnostic image. The imaging study can be decrypted and persisted in memory or remain encrypted and be persisted in memory. A transparent database encryption strategy could also be employed. Alternatively or in addition to the above options the disk on which the data lives can be encrypted using disk encryption.

The controller 362 is configured to confirm that the certificate authority which issued the token is a trusted entity and establish a secure communication session between the client device and the PACS server 3304. When the imaging request includes a request to retrieve a diagnostic image, the controller 362 fetches the diagnostic image from the PACS server 3304, and encrypts the diagnostic image to be sent back to the client device. When the imaging request includes a request to store a diagnostic image, the controller 362 decrypts the data to obtain the diagnostic image from the imaging request, re-encrypts the diagnostic image, associates the re-encrypted diagnostic image with the user name and stores the re-encrypted diagnostic image at the PACS server 3304. It should be noted that the order in which data is encrypted and decrypted may vary depending on the requirements of the system implementing the patient list manager. However, in most cases, the images can be encrypted in transit and a rest.

Referring to FIG. 3C, exemplary portions of a revenue cycle management (RCM) device 365 will be discussed. The RCM device 365 includes a transceiver 366, a controller 368 and a memory 370 including instructions for configuring the controller 368. The transceiver 366 can receive RCM requests from a client device and send the RCM requests to the patient list manager device 350 via the network 105. The RCM request can include a verification credential issued from a certificate authority (such as a token), a user name, and a request to associate a RCM attribute to one or more patient identifications in the patient list database.

The patient list manager device 350 is configured to confirm that the certification authority which issued the token is a trusted entity. If the token is confirmed, the controller 354 establishes a secure communication session between the patient list manager device 350 and the RCM device 365. The controller 354 can store the revenue attribute in the patient list database associated with the one or more patient identifications and activate a revenue attribute flag (denoting the stage of the patient revenue attribute in the RCM process) and one or more custom user determined tags (with meaning to one or a group of users, for example, particular RCM items a user desires to associate with one or more tags as a reminder that the RCM item needs additional input from a particular physician) associated with the one or more patient identifications.

The client device can access the RCM module by, for example, accessing a website hosted by a server associated with the RCM device or a client specific application. Similar to the administrative panel display, a RCM graphical interface can be available on the top level display to users with appropriate credentials or can be a separate application. The controller of the client device can be configured to generate RCM display when the RCM graphical interface is selected. The RCM display can include a plurality of RCM data entry graphical interfaces for entering RCM data relating to a service provided during a patient encounter and an RCM list view including one or more RCM events based upon the decrypted data.

Coders, office personnel, and 3rd party billing services that prepare claims for submission to payers for each billable episode of care a physician or other provider participates in often do not learn that billable care has been rendered until hours and often times several days after the care episode occurs. This potentially impacts physician and other providers adversely from a financial perspective by increasing the working capital tied up in their business via lengthening the time payables remain in their accounts receivable. The problem is further exacerbated when physicians and other providers see and treat patients in multiple potentially otherwise un-affiliated facilities separate from their home offices (i.e. inpatient hospital facilities) as there is no standard way for information about the care episodes physicians or other providers participate in to be transmitted back to their office for the billing of the professional services rendered. Currently, in many physician or other provider practices, manual processes and home grown solutions are used to fill this void or gap in communications and often consist of a patchwork of email, facsimile, or paper based correspondence (forms or cards brought to the point of care and carried by a physician or other provider back to those in their offices that do the billing for their services or to the 3rd party service providers they contract with for these services). Many of these manual home grown processes not only have a financial cost to the practice but also potentially are not in compliance with the patient privacy and data security regulations delineated in the Health Information Portability and Accountability Act of 1996, known as HIPAA.

Referring to the flow diagram of FIG. 39, a process for using the RCM module to add RCM attributes to the patient list database will be discussed. The RCM module can leverage structured data captured via the patient list manager about care episodes physicians and other providers engage in across multiple facilities to securely notify (in a HIPAA compliant fashion) office personnel (i.e. coders, billing managers, etc.) when a billable episode of care has occurred.

At 4202, one or more coders or coding team members (i.e. one or more coders, supervisors, and the senior managers) can be associated with a case based upon predetermined rules. Case can refer to a patient, a particular episode of care, or a combination of these or other patient attributes. As an example, the rules for determining the coder(s) to which an RCM item should be routed might include but are not limited to, the type of encounter, the clinical specialty involved, the facility, the provider, the procedure type, the disposition type, the date(s) of service, the patient, the insurance type, among many others.

At 4204, the RCM module is used to associate the case with a user name of the coder, and a RCM flag is set on the case. At 4206, the coder modifies an RCM attribute of the case and updates the RCM flag. The user could also annotate the RCM item with one or more custom tags (not shown on flow diagram; see screen shots, for example FIG. 40). At 4208, a status of the case can be updated to "Ready to Submit" which might put it into the queue for transmission to the payor and subsequently once it is sent, the status flag would be updated to "Submitted" either by a machine listening for the respective event or by the user. The RCM module can leverage structured data and annotations captured via the patient list manager which provides detail about each of the care episodes physicians and other providers engage in across multiple facilities, events which trigger secure notification (in a HIPAA compliant fashion) of office personnel (i.e. coders, billing managers, etc.) when a billable episode of care has occurred. Secure notification may include any number of communication means, including but not limited to, RCM module initiated SMS, email, push notifications to user devices, audio or tactile notifications, etc. Notification may be sent immediately upon each RCM item creation or edit event or batched based on number of newly submitted RCM items or elapsed time intervals. The system can also generate on demand user initiated secure notifications or messaging, for example between clinical providers and medical billing professionals. All notification content is sent over communication networks encrypted and is decrypted by the patient list client device where it is presented to the user. The notification content becomes an attribute of the patient and the RCM item and gets persisted in memory on the patient list device database and is encrypted at rest via data encryption, TDE or disk encryption. With RCM item information, notifications, and a solution for communication between collaborators, the billers and coders are able to efficiently move forward with the steps entailed in invoicing payors and/or patients for each billable episode of care. The data captured in the patient list manager provides a significant subset and sometimes all of the data needed by the coding and billing personnel for the claims preparation and submission process. The billers and coders utilize filters and query parameters including date ranges and other RCM item attributes to organize and view charges of interest facilitating their work flow. They can then review, edit and verify the accuracy of the RCM item and create the claim. The custom user tags allow them to manage their workflow at a more granular level than the RCM item status flags would alone. With the RCM module the status of any given RCM item (which itself or along with other RCM items becomes a claim in most cases) and the time it takes to be fully processed from the date the medical service was provided, to the time the RCM item is posted or submitted or entered into the practice management software (or claims submission solution used in the physician's or other provider's office), to the time a payment is received can be tracked and reported in real time. Performance statistics can be assessed or visualized versus target levels of performance and reporting can be generated for particular date ranges and at a variety of levels (i.e. individual, group or team, service line, business unit, facility, and hospital system or an aggregate group of physician group practices, etc.) and can be presented from a variety of perspectives which might be by clinical providers or by administrative back office users or via a view including both clinical providers and the non-clinical providers that work their RCM items. De-identified benchmarking data from other similar health care providers/health care provider organizations (for example similar in size or number of providers, similar specialty or subspecialty, similar region of the country, etc.) and focus can also be presented leveraging the network effect from the multi-tenant patient list manager offering or even be made available as a subscription for enterprise or private cloud installations. The RCM module increases the visibility of the practice's claims processing work flow an provides insights in to issues and developing challenging that might be impacting desired target performance, and it is capable of delivering this information in real time. In doing so the RCM module can drive ongoing, continuous improvement in the efficiency of the practice's financial or revenue cycle operations.

FIGS. 40-50 illustrate example displays generated by the RCM module. FIG. 40 shows an example inbox for a user. All charges shows all of the charges or RCM items a user is authorized to see which meet the 'routing criteria' (which charges go to which user—in this case a medical biller or a coder). Filters are hidden in this display. The tabs shown are custom user inboxes that are based off of saved user filter criteria. The status column includes system flag for indicating the status of the charge—the step it is in currently in the revenue cycle. In the tags column custom user determined tags that they want to use to filter charges on i.e. their 'custom' user inboxes can filter based on their user tags, for example.

Figure 42:
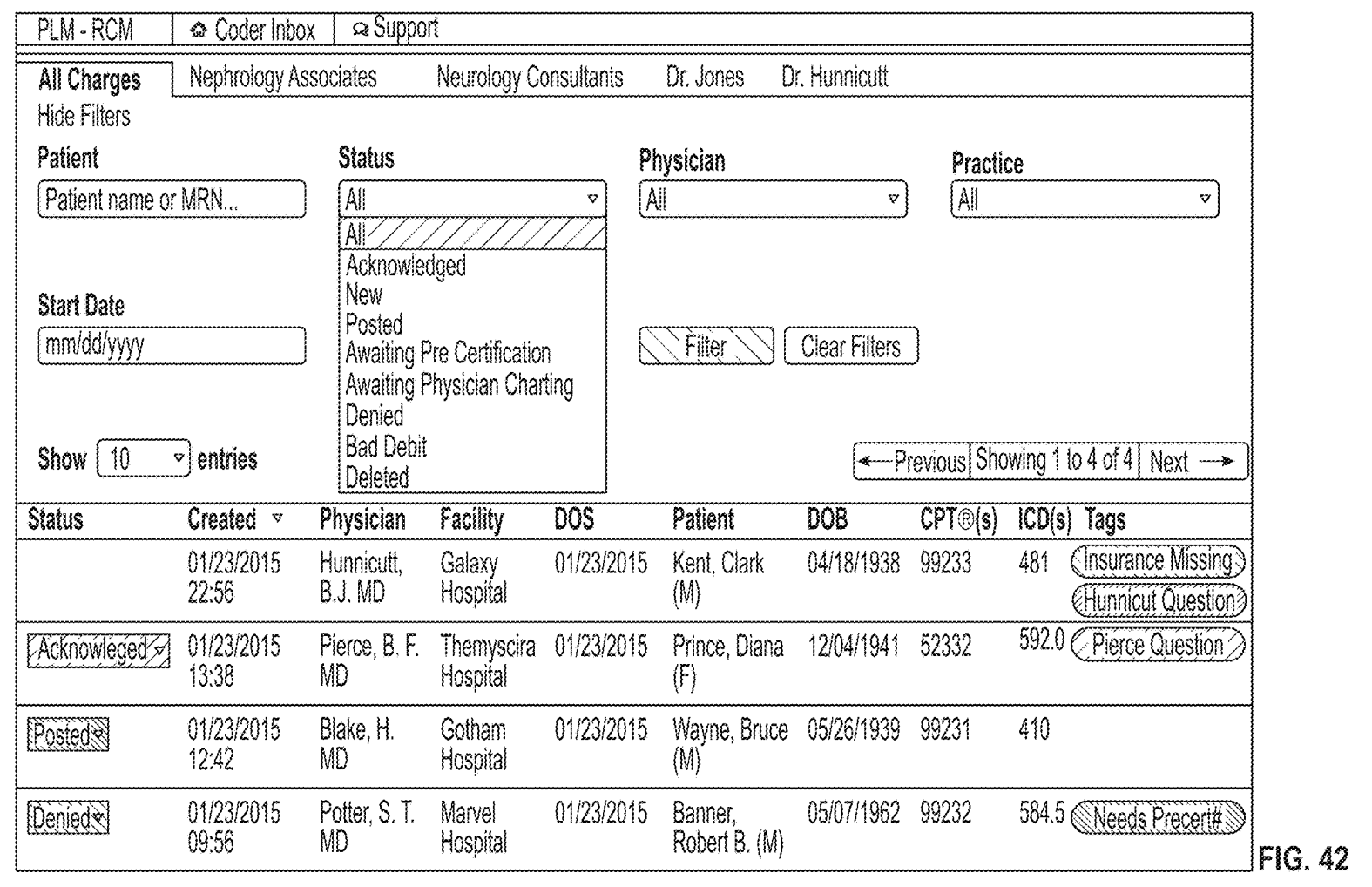
Figure 43:
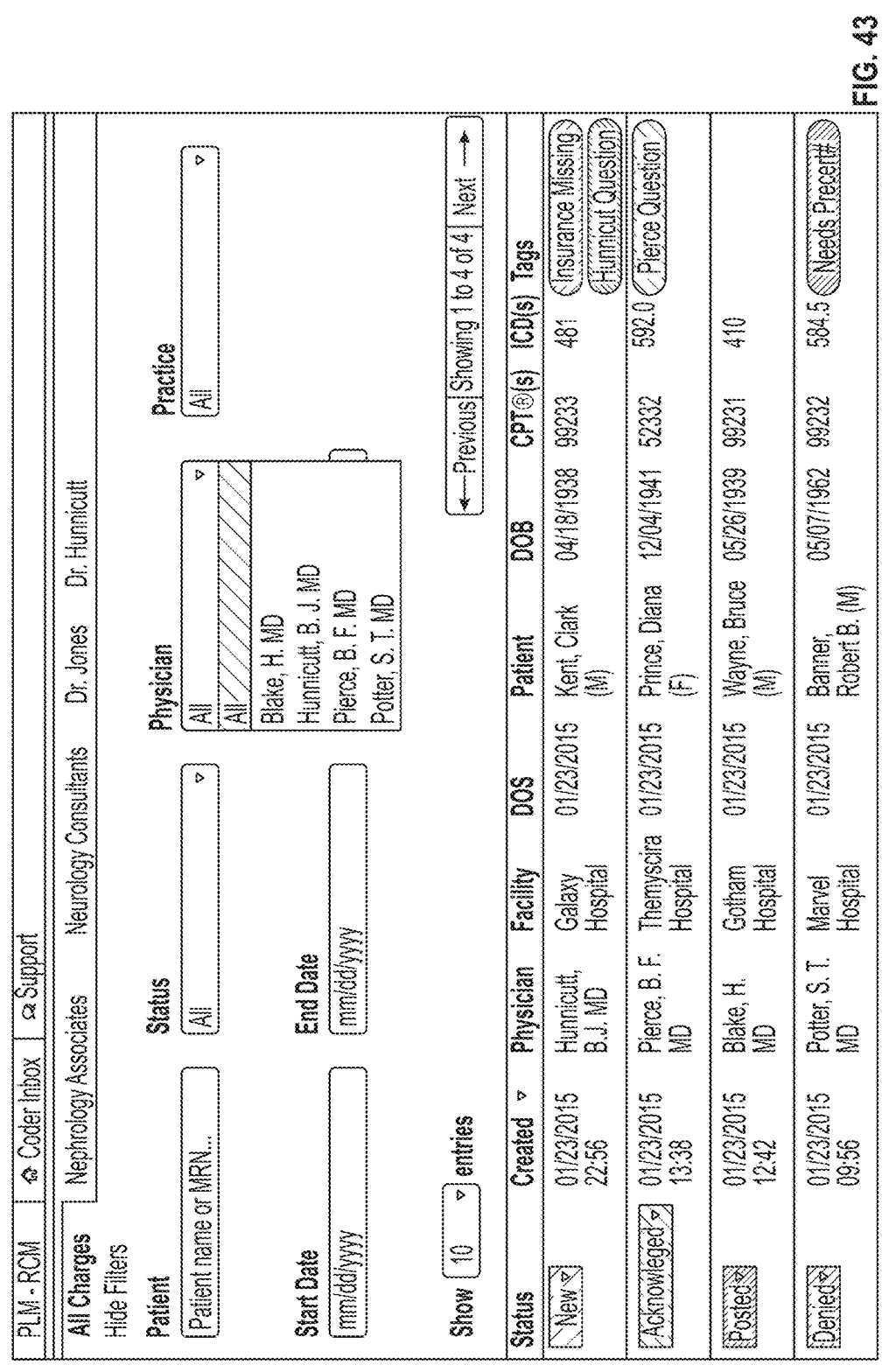
Figure 44:
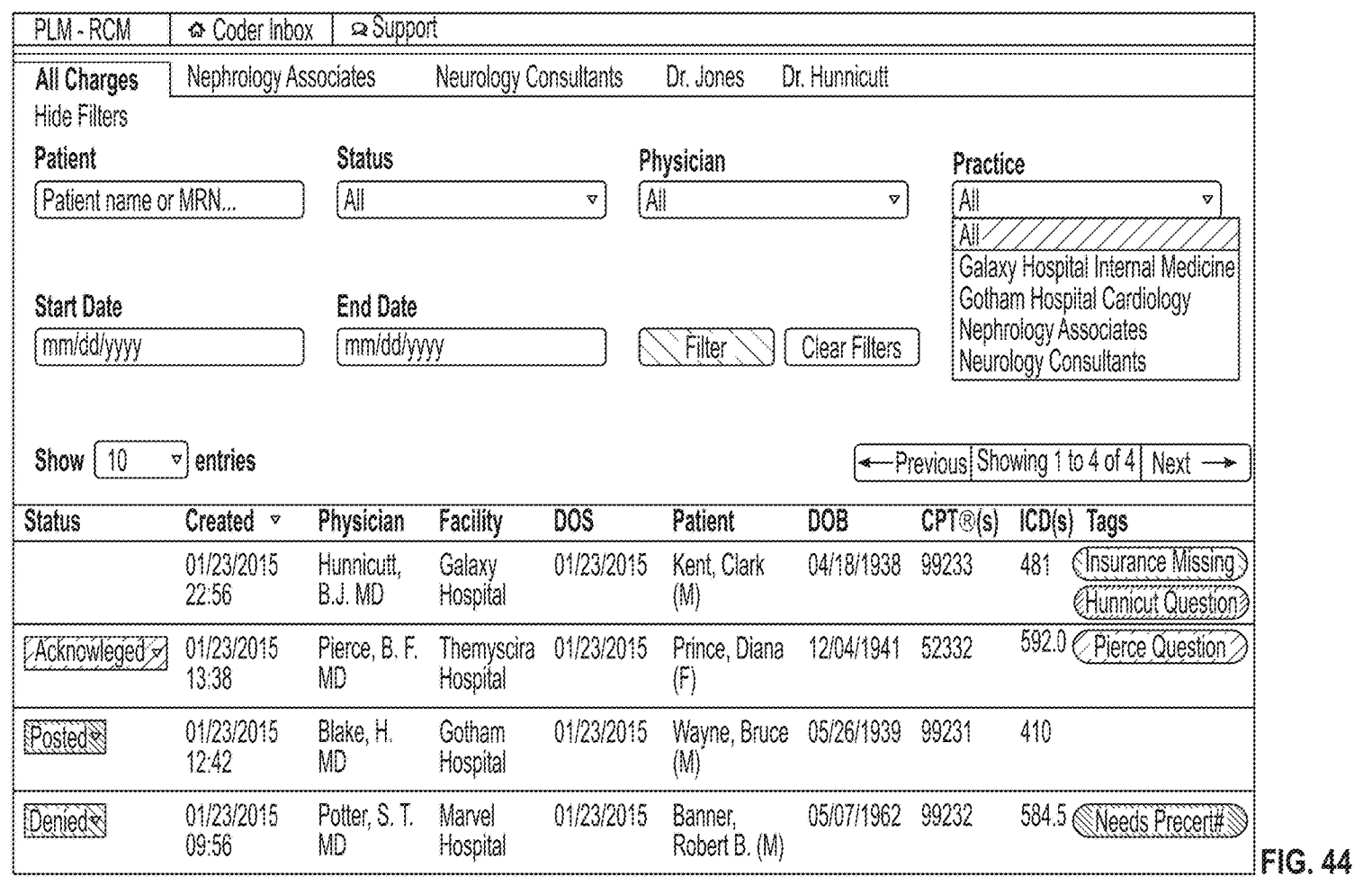

In FIG. 41, the filters are shown. Filters allow user to filter charges showing in the view. Note there are certain fields user can filter on including a free text search of patient name and medical record number (MRN). They can also filter the view by providing a range of dates between which they want to find charges. The date range can be for date of service (DOS) (shown) or for date of admission (not shown) or date of discharge (not shown); the system can also filter on start and end date. FIG. 42 shows the status drop down (can filter on one or more). FIG. 43 shows the physician drop down (can filter on one or more). FIG. 44 shows the practice drop down (can filter on one or more).

Figure 48:
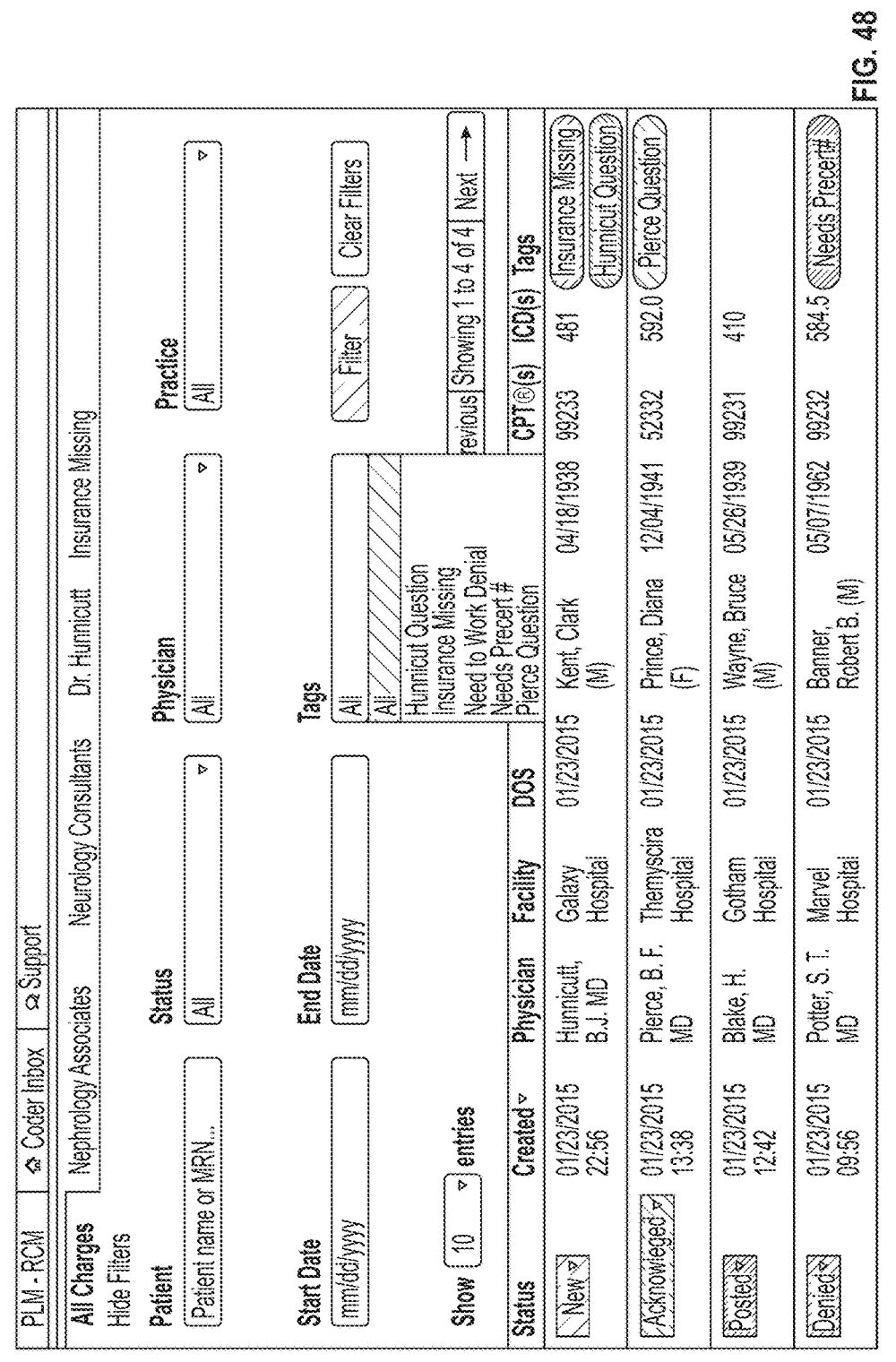
Figure 50:
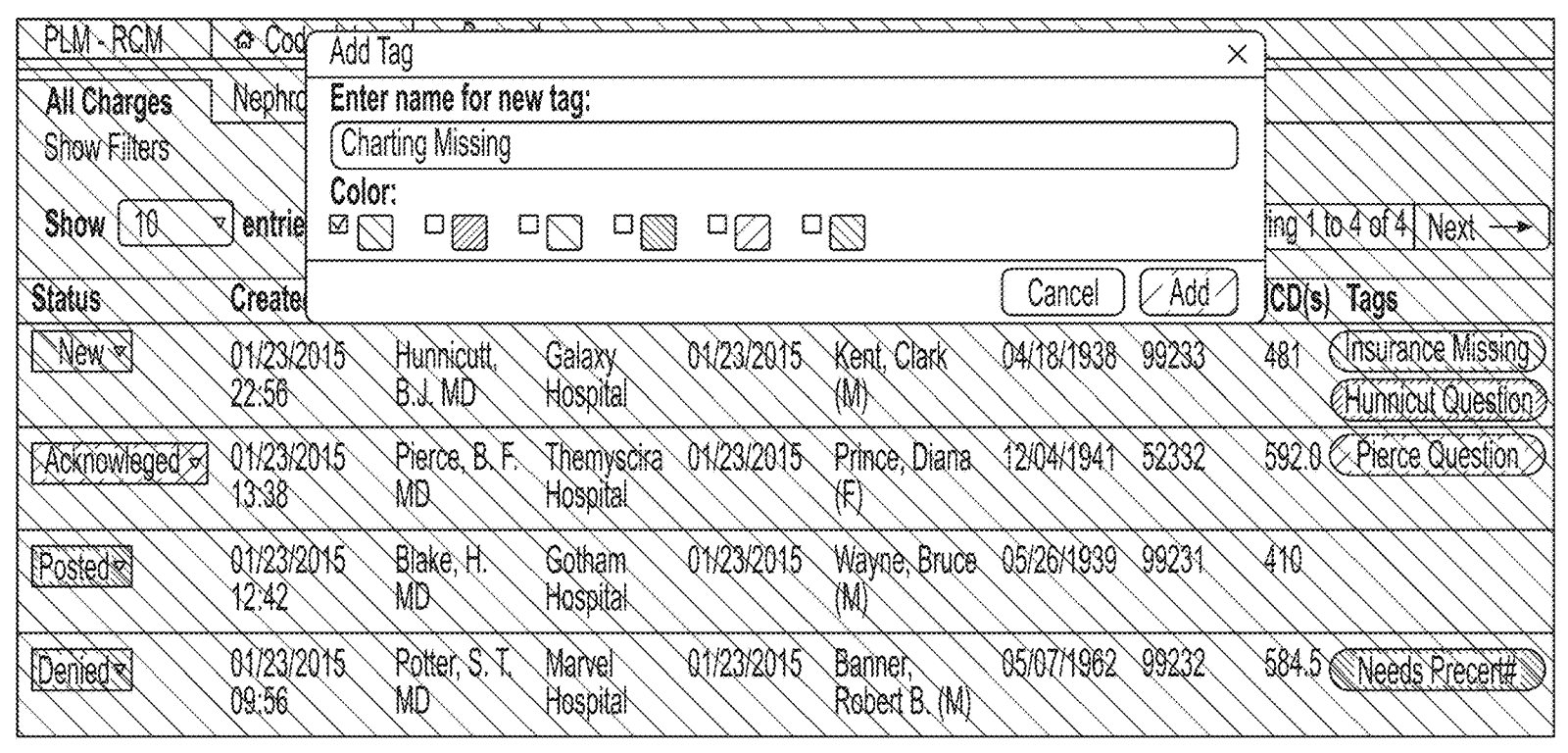

FIG. 45 shows a 'custom' user inbox based upon filters on practice name. FIG. 46 shows a 'custom' user inbox based upon filters on user 'custom' tag insurance missing. FIG. 47 shows how status can be updated from the master view. FIG. 48 shows filter on tags in inbox option turned on so that user can filter on one or more of their 'custom' tags. FIG. 49 shows an enlarged box to highlight plus button in tag column (how user adds a new 'custom' tag). FIG. 50 shows a modal dialog box showing the add 'custom' user tag user interface.

The patient list manager can include other modules besides those discussed above. For example, a clinical encounters dashboard outcomes and statistics reporting module can be included for generating a dashboard displays in a dashboard of statistics about clinical encounters physicians or other providers have participated in across one or more potentially unaffiliated facilities as shown in FIG. 41. The data statistics can be updated automatically in the dashboard in real time. The information is as up to date as the information last entered into the patient list manager database. No manual data collection, manipulation or calculations are necessary which eliminates a significant amount of the cost and time lag generating this information typically entails. These metrics can be securely accessed and used by physicians and other clinical providers, managers, executives and other subscribers for business intelligence and clinical intelligence. The data helps these subscribers more efficiently manage the activities and performance of individual, group or hospital owned physician practice and to readily assess their activities across multiple facilities on potentially disparate systems in one interface. Ultimately the data statistics and metrics reported can be used to improve patient outcomes and physician and other provider practice financial performance. Reports might include simple statistics for a subscriber specified date range such as clinical visit type volumes, surgical case types volumes and these respective volumes across facilities, by individual facility, by provider, by service line, etc. More complicated statistics requiring mathematical or algorithmic operations on data captured that are determined to be important can also be generated and output to the dashboard such as wound infection rates, readmission rates, etc. Any statistics and metrics that can be generated leveraging the structured point of care data captured can be output and made visible to subscribers with appropriate credentials in the dashboard in real time. If historical reports with particular statistics and metrics covering certain time periods or comparing certain time periods are desired, these can be generated and viewed in the graphical user interface or populated into a PDF which can be printed if a hard copy is desired. The statistics and metrics help increase the visibility of work flows, outcomes and volumes enabling subscribers to objectively understand and better manage (in real time or near real time) i) what is going on in their practice from a clinical and business operations standpoint, ii) practice and practice member productivity and performance versus targets; and iii) decision making around changes that might be made or implemented in the practice based on data driven impact assessment and key metric tracking and review.

Therefore, the present disclosure generally concerns a patient list manager system in which a client device accesses and stores patient data at a patient list database provided by a server via a connection to a network. The patient data is encrypted in motion (and at rest), and is accessible in the graphical user interface of a client device (which decrypts it) only with valid credentials (authentication via password). Data is populated into the system by a physician or other provider at any point of care or other location; the provider logs in with appropriate credentials via any web browser on any device or via a mobile device specific application (FIGS. 2, 4 and 36) and can then populate or abstract data into the system (FIG. 10) about patients they see and those they are actively managing (FIG. 5). Current encounters retain this status and are seen upon login (FIG. 5). The view can be filtered with a free text filter field or based on several criteria, including but not limited to provider, location of service, subspecialty group, among others (FIG. 6-8, FIGS. 37-38). When an encounter episode ends, the user updates the status and can categorize the disposition type; for example, a patient discharged from the hospital (FIGS. 16-18). In addition, care episodes can be flagged for future reference in the event some morbidity occurred and the provider wishes to be able to identify this subset of patients readily; free text notes can be captured about the care episode if flagged (FIG. 19). Patient episodes of care are captured in a structured fashion leveraging pull downs populated by look up tables. Limited free text is permitted for convenience to allow the provider to add custom notes of relevance (beyond that captured by the structured categorical designations), for example, diagnosis and procedure details (FIGS. 12-13) and to have this information displayed on the patient list (FIGS. 5 and 15). The list of current encounters can be viewed in the graphical user interface; or alternatively, a PDF can be generated (FIGS. 14-15) to view the information in order to provide consistent formatting should the user desire to print a 'hard copy.'

The patient list client device can be application stored locally at the client or accessed via a website. The patient list client devices request access resources from the patient list manager device(s). The patient list client devices do this by securely communicating via HTTP typically over SSL or TLS (with or without encryption of the actual content of the HTTP request being sent over SSL or TLS) with the patient list manager device and its modules via REST-like, RESTful, and/or RPC based APIs. The patient list manager device can be one or more virtual machine(s) on one or more servers which may interact with databases.

While only certain features of the invention have been illustrated and described herein, many modifications and changes will occur to those of ordinary skill in the art. The following claims are intended to cover all such modifications and changes.

What is claimed is:

1. A patient list manager client device comprising:
a transceiver for communicating with a patient list manager device via a connection to a network;
a controller coupled to the transceiver; and
a memory coupled to the controller, the memory including instructions to configure the controller to:
generate a resource request including an authentication credential associated with a user to be sent to the patient list manager device;
decrypt data received from the patient list manager device in response to the resource request, the data received from the patient list manager device being encrypted; and
generate a top level display based upon the decrypted data, wherein the top level display includes a patient list graphical interface, wherein a patient list display is generated when the patient list graphical interface in the top level display is selected, wherein the patient list display includes:
one or more graphical interface filters, each of the one or more graphical interface filters including a plurality of selectable patient attributes, wherein one or more identifications of patients and patient attributes associated with the one or more identifications of patients are displayed in the patient list display in accordance with patient attributes selected;
an add patient graphical interface;
wherein an add patient display is generated when the add patient graphical interface in the top level display is selected, the add patient display subsequent in hierarchy to the patient list display, the add patient display including:
an open text filter field for receiving data attributes of a patient to be added;
one or more classifying graphical interfaces including a plurality of selectable options for classifying the patient to be added, wherein the one or more classifying graphical interfaces includes encounter type graphical interfaces including encounter types for a care episode for the patient to be added and diagnosis graphical interfaces including diagnosis types for the care episode,
a procedure graphical interface for entering data relating to a new procedure or modifying data relating to an existing procedure, wherein the procedure graphical interface includes a graphical interface for entering a physician name, a role of the physician and selecting from a list of procedure types;
a remove patient graphical interface;
wherein a remove patient display is generated when the remove patient graphical interface in the top level display is selected, the remove patient display subsequent in hierarchy to the patient list display, the remove patient display includes a disposition type graphical interface including a list of disposition types for a care episode for a patient to be removed, a tag option for indicating a particular episode of care as a morbidity, and an open text field for providing additional details, and
the controller is further configured to generate an add patient request including parameters defined by the open text filter field, the one or more classifying graphical interfaces, and the procedure graphical interface, and a remove patient request including parameters defined by the disposition type graphical interface, the tag option and the open text field, the transceiver sends the add patient request and the remove patient request to the patient list manager device to process the add patient request and the remove patient request so that data in a patient list database is modified in accordance with the add patient request and the remove patient request and associated with the user, the data including the parameters of the add patient request and the parameters of the remove patient request.

2. The patient list manager client device of claim 1, wherein the one or more graphical interface filters of the patient list display include a first filter including a list of hospitals; and a second filter including a list of physicians and groups of physicians.

3. The patient list manager client device of claim 1, wherein the patient attributes displayed in the patient list display in accordance with patient attributes selected include a hospital or care facility associated with the authentication credential, and a type of unit or physician group associated with the hospital or care facility.

4. The patient list manager client device of claim 3, wherein:
the top level display further includes an administrative level graphical interface;
an administrative level display is generated when the administrative level graphical interface is selected, the administrative level display subsequent in hierarchy to the top level display, the administrative level display including an audit log graphical interface and a list of a plurality of top level parameters which can be modified,
wherein when the audit log graphical interface is selected, historical usage information is displayed;
wherein when one of the top level parameters is selected, a modification display for the one of the top level parameters is generated in which the selected one of the top level parameter can be modified, the modification display for each of the top level parameters including a graphical interface displaying respective data and a free text input field for filtering data displayed for the respective top level parameter.

5. The patient list manager client device of claim 1, wherein:
the top level display further includes an encounter query graphical interface;
a query engine interface display including query parameters for querying historical clinical encounters is generated when the encounter query graphical user interface is selected, wherein the query parameters include date ranges associated with procedures and admissions, encounter types, facility names, one or more physicians, disposition types and morbidity; and
the query engine interface display includes a results area in which information is displayed based upon the decrypted data received and received query parameters.

6. The patient list manager client device of claim 1,
the top level display further includes an images query graphical interface, and
wherein the controller is further configured to generate an upload screen for uploading a diagnostic image associated with a patient to the patient list manager or view one or more diagnostic images associated with the patient inside an embedded Digital Imaging and Communication in Medicine (DICOM) viewer.

7. The patient list manager client device of claim 1, wherein the controller is further configured to generate a revenue cycle management (RCM) display, the RCM display including a plurality of RCM data entry graphical interfaces for entering RCM data relating to a service provided during a patient encounter, an RCM list view including one or more RCM events based upon the decrypted data.

8. The patient list manager device of claim 1,
wherein the one or more memory sources include instructions for providing a resource available to the patient list client device via a plurality of REST-like, RESTful, and RPC based application program interfaces.

9. The patient list manager device of claim 1, wherein the verification credential includes an access token or a refresh token.

10. A patient list manager client device comprising:
a transceiver for communicating with a patient list manager device via a connection to a network;
a controller coupled to the transceiver; and
a memory coupled to the controller, the memory including instructions to configure the controller to:
generate a resource request including an authentication credential associated with a user to be sent to the patient list manager device;
decrypt data received from the patient list manager device in response to the resource request, the data received from the patient list manager device being encrypted; and
generate a top level display based upon the decrypted data, wherein the top level display includes a patient list graphical interface, wherein a patient list display is generated when the patient list graphical interface in the top level display is selected, wherein the patient list display includes:
an add patient graphical interface, wherein an add patient display is generated when the add patient graphical interface in the top level display is selected, the add patient display subsequent in hierarchy to the patient list display; and
a remove patient graphical interface, wherein a remove patient display is generated when the remove patient graphical interface in the top level display is selected, the remove patient display subsequent in hierarchy to the patient list display, the remove patient display includes a disposition type graphical interface including a list of disposition types for a care episode for a patient to be removed, and
the transceiver sends the add patient request and the remove patient request to the patient list manager device to process the add patient request and the remove patient request so that data in a patient list database is modified in accordance with the add patient request and the remove patient request and associated with the user, the data including a selected disposition type of the list of disposition types.

* * * * *